(12) United States Patent
Thorne, Jr. et al.

(10) Patent No.: US 7,101,354 B2
(45) Date of Patent: Sep. 5, 2006

(54) MIXING SYRINGE WITH AND WITHOUT FLUSH

(75) Inventors: Gale H. Thorne, Jr., Bountiful, UT (US); Gale H. Thorne, Bountiful, UT (US)

(73) Assignee: Infusive Technologies, LLC, Bountiful, UT (US)

( * ) Notice: Subject to any disclaimer, the term of this patent is extended or adjusted under 35 U.S.C. 154(b) by 0 days.

(21) Appl. No.: 11/359,304

(22) Filed: Feb. 21, 2006

(65) Prior Publication Data

US 2006/0142701 A1    Jun. 29, 2006

Related U.S. Application Data

(63) Continuation-in-part of application No. 11/284,504, filed on Nov. 22, 2005, which is a continuation-in-part of application No. 10/838,101, filed as application No. PCT/US05/14299 on Apr. 26, 2005, now Pat. No. 6,997,910.

(51) Int. Cl.
  *A61M 5/00* (2006.01)
  *A61M 5/315* (2006.01)

(52) U.S. Cl. ............................. 604/191; 604/231

(58) Field of Classification Search ............ 604/191, 604/218, 89–91, 184, 213, 226, 231, 237, 604/238, 523, 6.09
See application file for complete search history.

(56) References Cited

U.S. PATENT DOCUMENTS

| | | | |
|---|---|---|---|
| 3,976,068 A * | 8/1976 | Lundquist | 604/518 |
| 4,041,945 A | 8/1977 | Guiney | |
| 4,159,570 A | 7/1979 | Baskas et al. | |
| 4,479,578 A | 10/1984 | Brignola et al. | |
| 4,540,410 A | 9/1985 | Wood et al. | |
| 4,643,721 A * | 2/1987 | Brunet | 604/191 |
| 4,668,223 A * | 5/1987 | Grotenhuis | 604/191 |
| 4,792,329 A * | 12/1988 | Schreuder | 604/90 |
| 4,929,230 A * | 5/1990 | Pfleger | 604/90 |
| 5,080,649 A | 1/1992 | Vetter | |
| 5,122,117 A | 6/1992 | Haber et al. | |
| 5,171,220 A * | 12/1992 | Morimoto | 604/88 |
| 5,213,236 A * | 5/1993 | Brown et al. | 222/212 |
| 5,236,420 A * | 8/1993 | Pfleger | 604/122 |

(Continued)

OTHER PUBLICATIONS

Debiotech brochure from internet address www.debiotech.com (accessed May 25, 2004).*

*Primary Examiner*—Sharon Kennedy
(74) *Attorney, Agent, or Firm*—Gale H. Thorne

(57) ABSTRACT

A displaceable valved stopper is disclosed which partitions a conventional syringe into proximal and distal chambers to provide a multi-chamber, mixing syringe assembly. Also the valved stopper and a valve assembly are disclosed for use in a single conventional syringe to provide dual chamber mixing plus a disparate and sequentially dispensed flush. Incorporated in the valve assembly is another valved stopper and a separator which filters out gas from liquid being dispensed through the valve assembly. Each valved stopper is made as a single molded part which may be made from basic syringe plunger material. Also, each valved stopper may have a bi-state valve (e.g. a domed, slit valve). The separator is a single molded part which may be molded from basic syringe material. Each valve is actuated to a different state by differential pressure of a force greater than the associated valved stopper displacement force. A syringe plunger communicates through fluid in a more proximal chamber to force displacement of the valved stopper and valve assembly for both mixing and dispensing.

28 Claims, 12 Drawing Sheets

U.S. PATENT DOCUMENTS

| | | | | |
|---|---|---|---|---|
| 5,271,531 A | * | 12/1993 | Rohr et al. | 222/212 |
| 5,298,024 A | * | 3/1994 | Richmond | 604/90 |
| 5,489,266 A | | 2/1996 | Gremard | |
| 5,630,800 A | | 5/1997 | Blank et al. | |
| 5,695,465 A | * | 12/1997 | Zhu | 604/82 |
| 5,704,520 A | * | 1/1998 | Gross | 222/334 |
| 5,704,918 A | * | 1/1998 | Higashikawa | 604/191 |
| 5,713,857 A | * | 2/1998 | Grimard et al. | 604/82 |
| 5,743,886 A | * | 4/1998 | Lynn et al. | 604/191 |
| 5,743,890 A | * | 4/1998 | Hjertman et al. | 604/218 |
| 5,779,668 A | | 7/1998 | Grabenkort | |
| 5,785,682 A | * | 7/1998 | Grabenkort | 604/82 |
| 5,817,056 A | | 10/1998 | Tanaka et al. | |
| 5,830,193 A | * | 11/1998 | Higashikawa | 604/191 |
| 5,851,200 A | * | 12/1998 | Higashikawa et al. | 604/199 |
| 5,876,372 A | | 3/1999 | Grabenkort et al. | |
| 5,899,881 A | * | 5/1999 | Grimard et al. | 604/89 |
| 6,027,481 A | * | 2/2000 | Barrelle et al. | 604/187 |
| 6,045,004 A | * | 4/2000 | Elliott | 222/83 |
| 6,077,252 A | * | 6/2000 | Siegel | 604/214 |
| 6,120,478 A | * | 9/2000 | Moore et al. | 604/110 |
| 6,132,400 A | * | 10/2000 | Waldenburg | 604/191 |
| 6,142,977 A | * | 11/2000 | Kolberg et al. | 604/218 |
| 6,149,628 A | * | 11/2000 | Szapiro et al. | 604/191 |
| 6,161,364 A | * | 12/2000 | Kolberg | 53/425 |
| 6,171,220 B1 | * | 1/2001 | Lumpkin | 482/105 |
| 6,234,190 B1 | | 5/2001 | Fisher et al. | |
| 6,267,154 B1 | | 7/2001 | Felicelli et al. | |
| 6,419,656 B1 | | 7/2002 | Vetter et al. | |
| 6,544,233 B1 | * | 4/2003 | Fukui et al. | 604/191 |
| 6,602,223 B1 | * | 8/2003 | Szapiro et al. | 604/89 |
| 6,622,721 B1 | * | 9/2003 | Vedrine et al. | 128/200.19 |
| 6,641,561 B1 | * | 11/2003 | Hill et al. | 604/136 |
| 6,723,074 B1 | * | 4/2004 | Halseth | 604/201 |
| 6,740,062 B1 | * | 5/2004 | Hjertman | 604/187 |
| 6,866,653 B1 | * | 3/2005 | Bae | 604/191 |
| 7,001,362 B1 | * | 2/2006 | Vincent | 604/191 |
| 2002/0192113 A1 | * | 12/2002 | Uffenheimer et al. | 422/67 |

\* cited by examiner

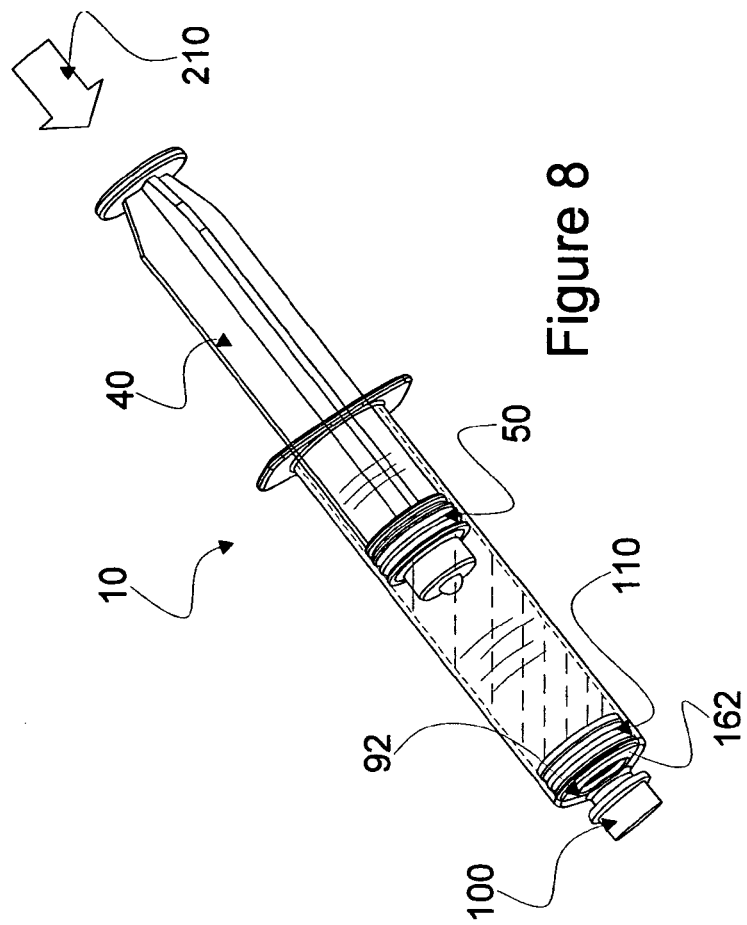
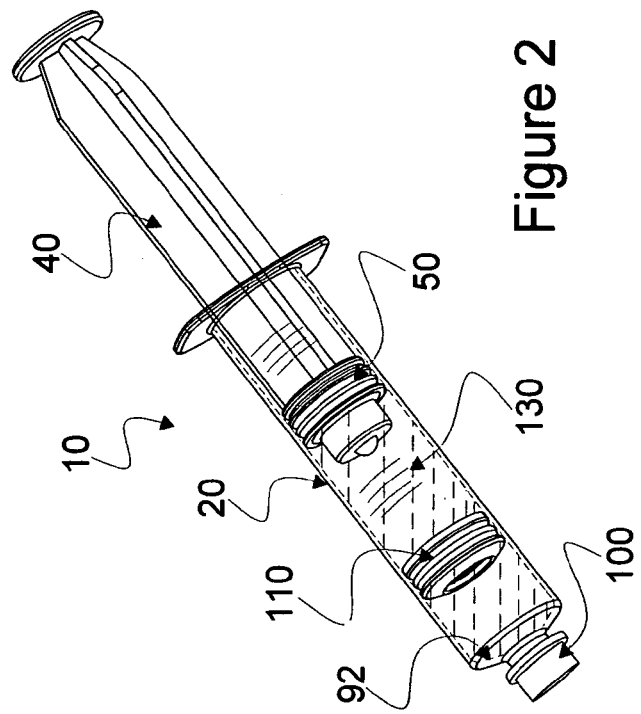

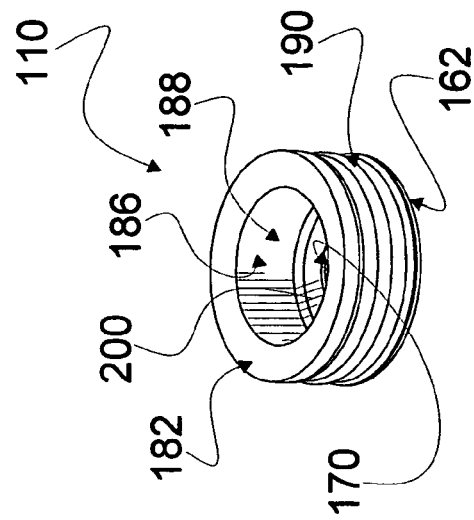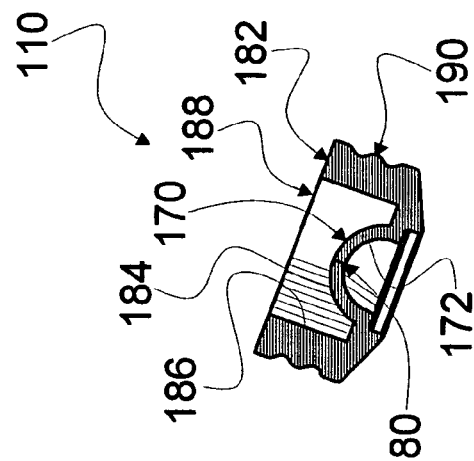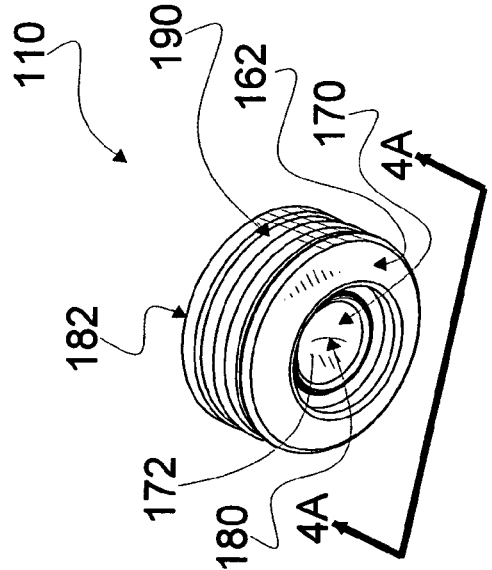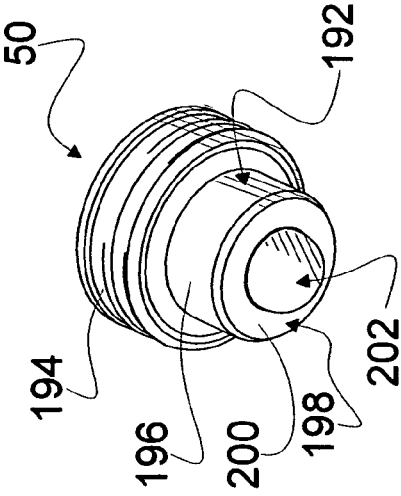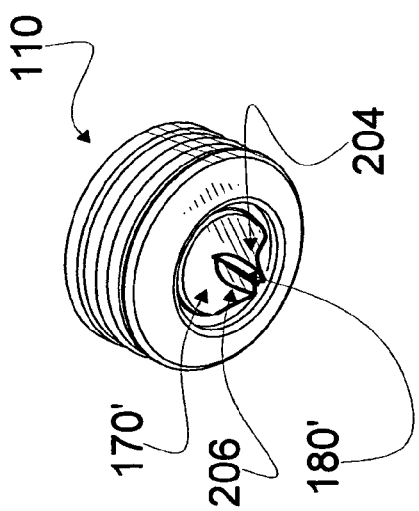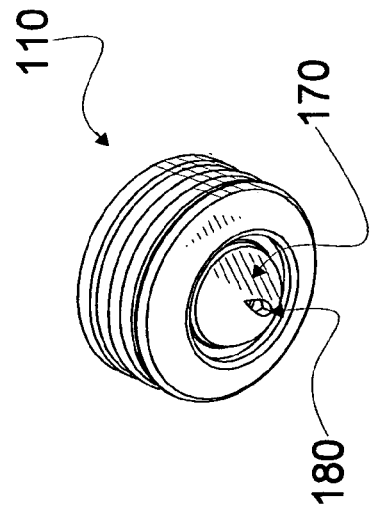
Figure 4
Figure 4A
Figure 5
Figure 6
Figure 6A
Figure 7

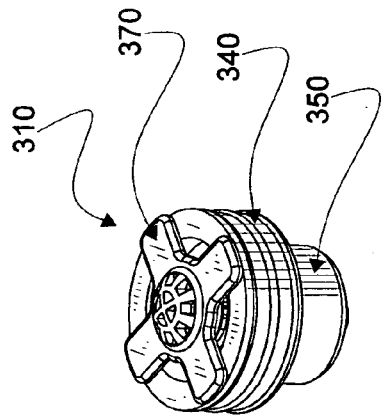
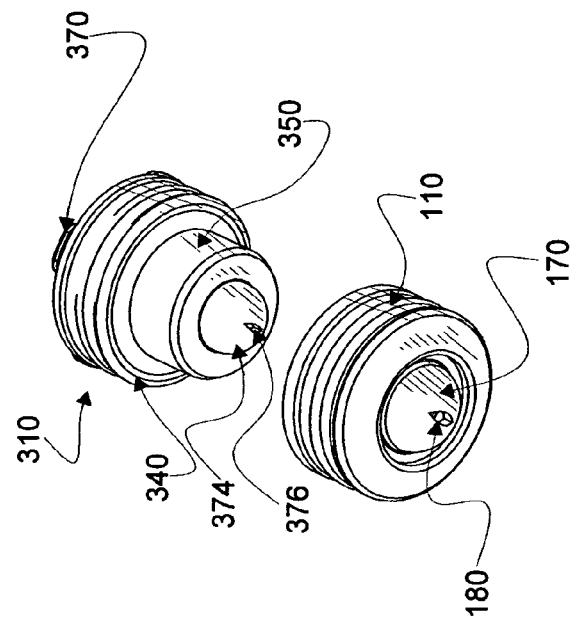
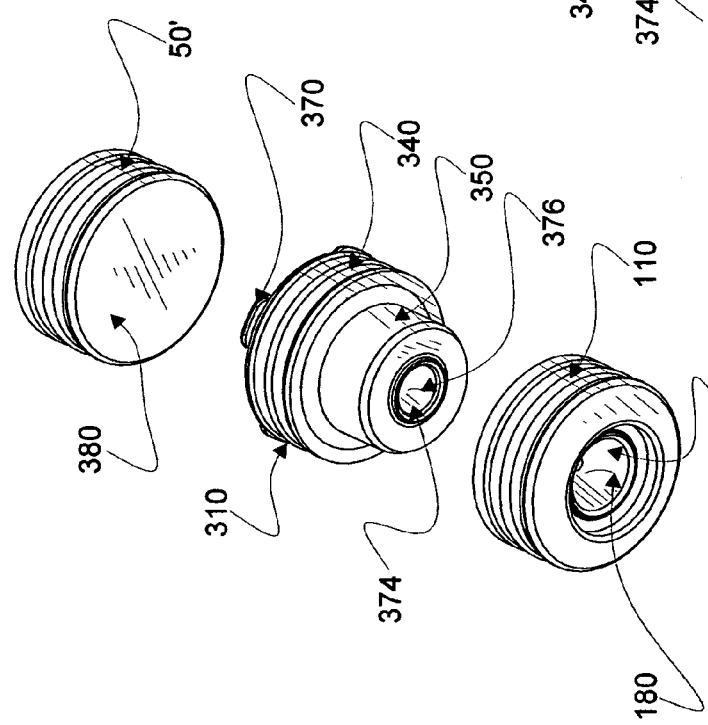

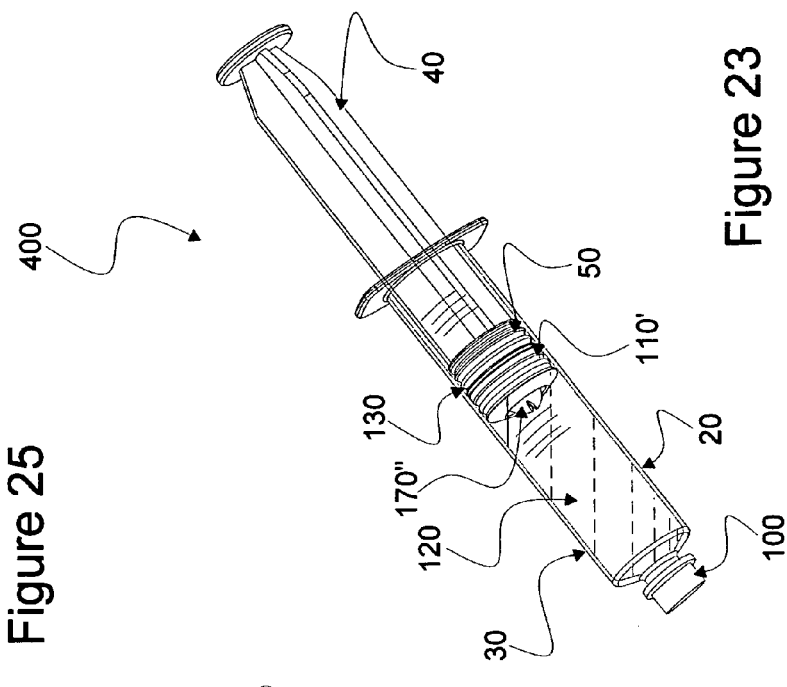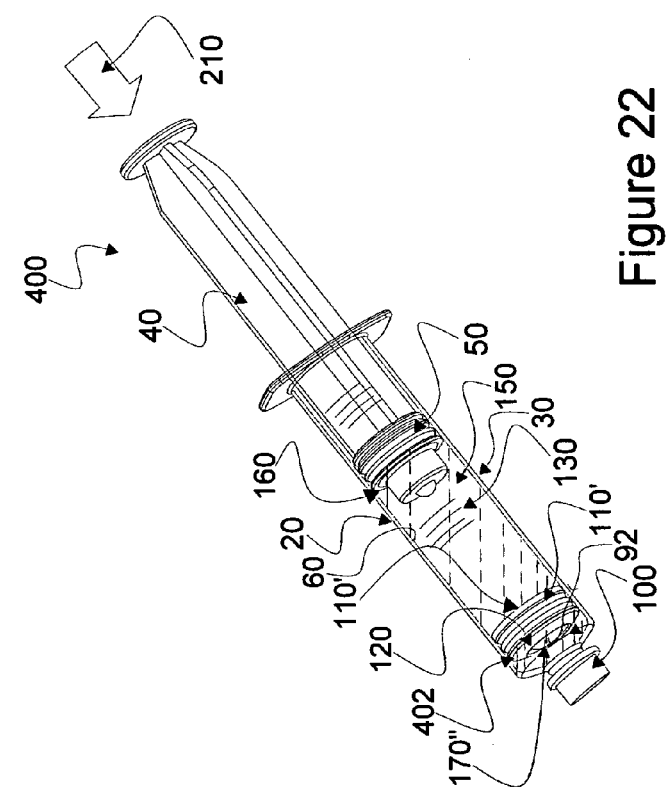

MIXING SYRINGE WITH AND WITHOUT FLUSH

CONTINUATION-IN-PART

This Patent Application is a Continuation-in-Part of U.S. patent application Ser. No. 11/284,504 titled MULTI-CHAMBER, SEQUENTIAL DOSE DISPENSING SYRINGE, filed by Gale H. Thorne, Jr. et al. (Thorne, Jr.) on Nov. 22, 2005; which is a Continuation-in-Part of U.S. patent application Ser. No. 10/838,101, titled MULTI-CHAMBER, SEQUENTIAL DOSE DISPENSING SYRINGE, filed by Howlett, et al. (Howlett) on May 3, 2004, for which a U.S. Pat. No. 6,997,910 has been issued, and, for which an international PCT patent application number of PCT/US05/14299 was filed Apr. 26, 2005.

FIELD OF INVENTION

This invention relates to mixing syringes and multi-chamber syringes and, in particular, to mixing syringes which utilize conventional syringe barrels and, in the case of multi-chamber flush syringes, dispense fluid from each chamber sequentially.

DESCRIPTION OF RELATED ART

This invention is a Continuation-in-Part of Thorne, Jr. which discloses multi-chamber syringes which can be used for sequential delivery of fluids. As this instant invention can involve a combination of both a mixing syringe and a sequential fluid delivery application, contents of Thorne, Jr. are included herein by reference.

Syringes for storing and mixing materials comprising diluents in one chamber and either dry (e.g. lyophilized) or liquid reagents (e.g. medications) in a disparate chamber are well known. Such syringes provide a means for mixing, while both materials are kept disparate within the syringe prior to use. Achieving a mixing syringe in current art has taken many forms, including frangible diaphragms, special barrel geometries which permit fluid flow between chambers when a separating stopper is displaced to a predetermined slotted or expanded portion of a barrel, telescoping barrels and plugs. Often some type of special barrel design is utilized. Beyond the requirement for special barrel design, there may be performance issues associated with such syringes, such as dead space and numbers of mixing syringe parts and complexity.

As an example, U.S. Pat. No. 4,041,945 titled MIXING SYRINGE and issued to Aeneus C. Guiney Aug. 16, 1977 (Guiney) discloses mixing syringe apparatus which employs a conventional syringe barrel. One chamber for a diluent is disposed in the syringe barrel. A chamber for material to be diluted is disposed in a chamber formed in a resilient piston head. It is noted that such a mixing syringe limits volume of material which can be diluted and establishes a dead space relative to a delivered volume.

Generally, within each serial delivery syringe, chambers are separated by an intermediate sliding stopper or other part which receives motive force communicated through an intermediate fluid from a primary stopper which is part of a plunger assembly and against which an external force is applied. For disparate fluids to be dispensed sequentially or serially, each intermediate stopper must provide a fluid-tight seal to assure that no inadvertent chamber-to-chamber communication occurs and that all fluid from a distal chamber is evacuated from the syringe before dispensing fluid from a more proximal chamber. Once the distal chamber of the syringe is so purged, that intermediate stopper must be breached or bypassed to permit dispensing of the contents of a proximal or intermediate chamber.

Definition of Terms:

Following is a brief list of clarifying definitions for terms used in this Application:

assembly n: a device which is made from at least two interconnected parts barrel n: a cylindrical elongated portion of a syringe which is conventionally open on one end to receive a plunger and stem used for displacing fluid within the barrel and partially closed at an opposite end except for an orifice through which fluid is ejected or aspirated bi-stable adj: a descriptor for a device having two stable states clinch n: a structure or device which acts upon a part to clamp it closed while in contact therewith conventional adj: sanctioned by general custom; i.e. commonplace, ordinary chamber n: a volumetric portion of a divided barrel disparate n: when used in conjunction with a liquid volume, a volume of liquid which is distinctly separate from another liquid volume differential pressure ($\Delta P$) n: a pressure gradient resulting from unequal pressures exerted upon opposing sides of a structure; generally as used herein, $\Delta P = P_p - P_d$ distal adj: a term which depicts placement away from a reference point (e.g. away from a user of a syringe)

dome n: an arcuately shaped surface (e.g. a hemisphere)

downstream adj: a direction which is consistent with flow out of a syringe or away from a user fluid n: a substance (e.g. a liquid and/or gas) which tends to take the shape of a container front adj/n: distally disposed or a distally disposed site (e.g. a front of a syringe comprises the dispensing orifice)

gas n: a fluid which is neither solid nor liquid liquid n: a fluid which is neither solid nor gaseous, generally considered to be free flowing like water non-planar adj: not planar in a resting or stable state medial adj: occurring away from an outer edge; disposed near the center of (e.g. disposed away from an edge or periphery and in the vicinity of a center of gravity or axis of symmetry)

$P_d$ n: pressure in a distal chamber or a pressure which is distally disposed relative to a structure across which a differential pressure is effected plunger n: a portion of a syringe piston apparatus usually affixed to a syringe stem which is used to displace fluid within a syringe barrel prime v: to fill liquid into a cavity generally by removing air therefrom (e.g. priming a gas separator)

$P_p$ n: pressure in a proximal chamber or a pressure which is proximally disposed relative to a structure across which a differential pressure is effected proximal adj: opposite of distal (e.g. a term which depicts placement nearer than a reference point)

rear adj: opposite from front (i.e. generally associated with a part of a syringe barrel which is proximal to a syringe user)

reflux n: a type of undesired retrograde (upstream) flow of liquid (e.g. blood into a catheter or the like) from a vessel in which the catheter or the like resides separator n: a liquid filter which impedes passage of air while permitting liquid to flow through the separator state n: mode or condition of being; when referenced to a valve assembly, a condition which permits or restricts fluid flow under predetermined conditions stiction n: a special case of friction; stiction being the force required to initiate motion to a resting body, esp. when stiction is greater than moving friction stem n: an elongated part which fits within a syringe barrel and is affixed to a plunger for the purpose of displacing fluid within the barrel stop n: a obstruction which is differentiated from friction or stiction, esp. an obstruction which halts displacement of a stopper or plunger stopper n: a stem-free plunger associated with a stopper assembly or mixing syringe assembly, in the instant invention, each stopper contains a self-actuating valve syringe n: a device used for injecting or withdrawing fluids upstream adj: a direction which is against the direction of flow from a syringe (opposite of downstream)

BRIEF SUMMARY AND OBJECTS OF THE INVENTION

In brief summary, the currently preferred embodiment of this novel invention alleviates all known problems related to providing an effective mixing syringe assembly and, further, a mixing syringe assembly and multi-chamber, sequential dose dispensing syringe combination.

Generally, the invention employs a syringe of traditional design which has a conventional hollow barrel having an elongated internal cylindrical surface, the barrel surface comprising an open proximal end and a distal end having a closed interior about an orifice through which fluid is transferred, and a stem and plunger combination, the combination being disposed to be displaced within said barrel, for mixing, by application of force, in a predetermined direction, against the stem, thereby imposing differential pressures which displace fluid within the barrel.

During mixing, a removable cap is disposed about the orifice and, in combination with the plunger, fully confines all fluid and material previously stored within said syringe barrel between the plunger and cap.

A displaceable valved stopper is disposed within the barrel between the plunger and the distal end to provide a more proximal chamber disposed between the plunger and the valved stopper, thereby providing a container for a first volume of matter, and a more distal chamber, disposed between the distal end and the valved stopper as a container for a second volume of matter. The first and second volumes of matter are thereby kept disparate before mixing. Mixing is accomplished by action of forcing displacement of the stem in the predetermined direction.

The displaceable valved stopper comprises a normally-closed valve which yields to an open state when the predetermined pressure differential is disposed across the valved stopper. Orientation of the valve determines direction of application of force upon the stem to open the valve. That pressure differential which opens the valve causes fluid flow to be dispensed through the valve, thereby mixing fluid from one chamber (the dispensing chamber) with fluid resident in the other (receiving) chamber.

Of critical importance is containment of an elastic fluid within the more distal chamber wherein energy, resulting from pressure derived from force applied in the predetermined direction upon the stem of the syringe, is stored. At least a portion of the stored energy effects displacement of the valved stopper in a direction opposite direction of the applied predetermined force once that force is terminated, thereby changing size of one chamber relative to the other chamber and providing opportunity for additional dispensing of fluid through the valve by subsequent application of force in the predetermined direction.

In this manner, by repeated application of force on the stem in the predetermined direction, substantially all matter in one chamber is displaced into the other chamber to accomplish mixing. Prior to mixing it is critical that contents of the two chambers remain disparate. For this purpose, a biasing memory element may be provided. Such a biasing memory element may be provided in place of the stem within the barrel of the syringe prior to mixing. The biasing element maintains a differential pressure across the valved stopper which keeps the valve closed during shipping, storage and before use.

Further, in a combination embodiment a valve assembly like the valve assembly disclosed in Thorne, Jr. is disposed between the valved stopper and plunger to divide the more proximal chamber into a middle chamber and a most proximal chamber. The middle chamber acts as the more proximal chamber the previous embodiment described. The most proximal chamber is filled with a fluid which may be used as a flush. All three chambers retain matter disparate until used. Fluid from the most proximal chamber is dispensed separately and sequentially following mixing and dispensing of mixed fluid from the distal and middle chambers. Of course, the cap is removed prior to dispensing fluids from the syringe. Dispensing is accomplished by conventional application of force upon the stem.

More specifically, in a first basic embodiment, the invention involves at least one (first) distally disposed displaceable valved stopper which is designed to operate within a conventional syringe to separate a most distal chamber from a more proximal chamber.

In this first embodiment, before dispensing, the distal chamber generally contains a first fluid volume, which may be a diluent; however, in a second basic embodiment, the distal chamber may contain a mass or other material to be diluted. The adjacent, more proximal chamber contains a disparate second fluid volume or mass of material.

In the first embodiment, an initial state of a closed valve in the first stopper keeps the contents of each chamber separate from the other until initiation of a mixing step. A cap which seals the syringe against influent or effluent fluid flow is disposed to block fluid flow in or out of the syringe until the mixing step is complete. In this first embodiment, a plunger affixed to a stem of the syringe is used as a forcing tool both in mixing and in dispensing fluids from the syringe. Generally, the plunger communicates force, applied against the syringe stem, to the valved stopper through an intermediate fluid.

Preferably, the distal face of the valved stopper is shaped to correspond to the internal shape of the distal end of the syringe to minimize dead space. All parts which communicate with the proximal side of the valved stopper are also shaped to nest or otherwise correspond to the proximal side of the valved stopper to similarly minimize dead space.

The valve in the first valved stopper has several important and critical features. First, the valve remains absolutely closed in a first state when a first positive $\Delta P$ (a zero $\Delta P$ being considered positive) is disposed across the valve, thus keeping fluid or other matter in the chambers disparate during shipping, storage and prior to mixing.

Second, the valve in the first valved stopper is designed to become patent to flow of fluid, in the first state, from the distal chamber into the proximal chamber when a negative $\Delta P$ is imposed across the valved stopper by proximal displacement of the stem and plunger within the barrel of the syringe. When imposing such a negative $\Delta P$ upon the valved stopper, it is critical that a portion of the fluid in the distal chamber be gas (e.g. air) to provide an elastically expandable and compressible component therein.

Thus, when the stem of the syringe is forcibly displaced proximally, fluid is withdrawn from the proximal chamber through a patent valve of the first valved stopper. At the time fluid is being withdrawn from the distal chamber, pressure in the distal chamber is negative relative to ambient pressure outside the syringe. Once force is relieved from the stem, a resulting change in pressure causes the valve to close, and the first valved stopper is resultingly distally displaced by the resulting pressure gradients among the distal, and proximal chamber(s) and ambient pressure outside the syringe. Repeated application of proximally directed force and resulting proximal displacement of the stem ultimately "pumps" substantially all fluid from the distal chamber and, thereby, displaces the valved stopper to abut the internal distal face of the syringe with substantially all of the fluid originally disposed in the distal chamber being displaced to mix with fluid in the more proximal (mixing) chamber.

Once the fluids are mixed in the proximal chamber in the first embodiment, the mixed fluids may be directly dispensed or further mixed by an alternate step. For the alternate step, a distally directed force is imposed upon the stem to create a predetermined positive switching pressure gradient across the valved stopper while the valved stopper is abutting the internal distal face of the syringe. Such a pressure gradient causes the valved stopper to be switched to a second state which is permissive to distally directed fluid flow through the valve. Also, for further mixing to occur, the valve in the second state must then restrict proximal fluid flow when force is relieved from the stem. In such a case, each time distally directed force is applied to the stem, after the valve is switched to the second state, fluid is pumped from the proximal chamber through the valve into the distal chamber to abet additional mixing.

Once either mixing step is complete (and the cap is removed), a distally directed force is applied to the stem, then, by conventional procedures, gas (i.e. usually air) is primed from the syringe followed by dispensing of mixed liquid.

In the case of the mixing syringe assembly and multichamber, sequential dose dispensing syringe combination, two valved stoppers are employed. The more distal stopper is the same as the first valved stopper disclosed supra. The second or more proximal valved stopper is part of a stopper assembly, an example of which is disclosed in Thorne, Jr., incorporated herein by reference. The two stoppers divide the barrel of the syringe into three chambers. The most distal two chambers perform the same storage and mixing functions disclosed for the mixing syringe assembly disclosed supra. The third and most proximal chamber is generally used for storing a third disparate fluid, such as, for example, a flush solution.

As disclosed in Thorne, Jr., the stopper assembly comprises two elements, the second valved stopper and a stopper stabilizer and gas separator (referenced hereafter as a "separator"). The valved stopper contains a valve mechanism held closed by a clinch and is only actuated by a predetermined positive pressure differential across the valve. Thus, the stopper assembly may be displaced proximally by action against the stem and associated plunger to "pump" fluid from the distal chamber into the next more proximal chamber (which is the mixing chamber) as disclosed supra. Because the valve of the valve assembly only opens when displaced to collide with a more distal end of the syringe (or another stop within the syringe such as against the first valved stopper), solutions contained in the mixing chamber and in the most proximal chamber are kept disparate during mixing and dispensing of the mixed solution. Only after the mixed solution is fully dispensed (when the valve assembly collides and nests against the first valved stopper) does the valve of the second valved stopper open. Thus, the following steps are achieved:

1. The syringe stem and plunger are drawn proximally and released until contents of the most distal chamber are displaced for mixing into the middle chamber.

2. The contents of the most distal chamber and middle chamber are allowed to reside in the middle chamber for a predetermined period of time to assure adequate mixing.

2.a. By an alternate switching of the first valved assembly valve to a second state, contents of the middle chamber are permitted to be pumped into the most distal chamber for further mixing.

3. The cap is removed.

4. Consistent with conventional protocol, the chamber holding the mixed fluid is purged of air.

5. The syringe is connected to a dispensing site.

6. The syringe stem and plunger are displaced distally to dispense liquid from the mixing chamber.

7. Once the mixing chamber is empty (the valve assembly is nested against the first valved stopper), the valve, of the valve assembly, is opened by an increased positive $\Delta P$ (force against the stem and plunger) and content of the most proximal chamber is dispensed.

Note that, one basic difference between the valved stopper disclosed in Thorne, Jr. and the second valved stopper is that, rather than contouring the distal face of the second valved stopper to correspond to the inner distal face of the syringe barrel (as taught in Thorne, Jr.), the distal face of the second valved stopper is contoured to nest within the proximal side of the first valved stopper to minimize dead space as the mixed solution is dispensed from the syringe prior to actuation of the valve in the second valved stopper for the purpose of dispensing fluid from the most proximal chamber.

Notably, mixing occurs by applying force upon the syringe stem in one direction which results in displacement of a valved stopper in a direction opposite the direction of a force applied to a stem of the syringe. For this reason, a second embodiment of the instant invention involves a valved stopper having a normally-closed valve which is permissive to distal flow when a positive differential force is applied across the valved stopper. Thus when a positive force is imposed upon the syringe stem fluid is forced distally through the normally-closed valve and, once the force is removed, equilibrating pressures force the valved stopper proximally. Thus, in this second embodiment, diluent is stored in a more proximal chamber and medical matter to be diluted is disposed in the distal chamber. Successive imposition of force producing a positive pressure differential across the valved stopper displaces fluid from the more proximal chamber to the distal chamber where mixing occurs.

In all embodiments of Thorne, Jr. and this instant invention, action upon a plunger associated with the syringe communicates through the most proximal volume of fluid to displace syringe stopper assemblies. In those valved stoppers employing bi-state or bi-stable operation, once each valved stopper is displaced to abut a stop, a resulting positive $\Delta P$, causes the associated valve in the abutting valved stopper to open to permit dispensing of liquid from the chamber which is just proximal from that valved stopper.

Upon complete evacuation of the liquid from that proximal chamber and by collision of the next valved stopper with the distal internal end surface of the syringe (or another stop), a positive differential pressure across the stopper resulting from force against the syringe stem causes the valve in the next valved stopper to be opened to a second state. Thus, continuous action upon the stem of the syringe permits sequential and selective dispensing of liquid contents from each such proximal chamber following dispensing of fluid from each more distal chamber. In the embodiment where mixing is dependent upon a positive differential pressure, there is no need to switch an associated valve to a second state, as the valve is already open to dispense fluids from the syringe.

It is important to note that conditions which inhibit reflux, guard against dispensing gas from the most proximal chamber, maintain stability of the valve assembly as it is displaced within a syringe barrel and assure low resistance to dispensing flow in the mixing syringe assembly/multi-chamber syringe combination are the same as for the multi-chamber syringe, disclosed in Thorne, Jr.

Accordingly, it is a primary object to provide a displaceable valved stopper which partitions a conventional commercial syringe to make a mixing syringe assembly.

It is a fundamental object to provide a valved stopper for a syringe which keeps two disparate fluids apart until the fluids are mixed by force delivered upon a plunger associated with a stem of a syringe.

It is another fundamental object, in a first embodiment, to provide a displaceable valved stopper which has a valve which, in a first state, becomes patent to fluid flow when a negative $\Delta P$ is disposed across the valved stopper.

It is yet another fundamental object, in a second embodiment, to provide a displaceable valved stopper which has a valve which, in a first state, becomes patent to fluid flow when a positive $\Delta P$ is disposed across the valved stopper.

It is an extremely important object to provide a valved stopper and associated fluid delivery parts within a syringe which yield a low dead space for dispensed liquid.

It is another important object to provide a valved stopper having an operable slit valve.

It is an object to provide a bi-state valve as part of a valved stopper.

It is a very important object to provide a mixing syringe assembly and multi-chamber syringe combination having three disparate chambers.

It is an object to provide a mixing syringe assembly which has a chamber, which ultimately contains a mixed solution, which can be purged of air prior to medication delivery.

It is another primary object to provide a valve assembly which opens to dispense liquid from a most proximal chamber only after liquid from a more distal chamber has been dispensed.

It is a basic object to provide a valve assembly which acts as a liquid filter in the most proximal chamber to deter gas in a flush solution from being dispensed from the most proximal chamber.

It is a very important object to provide a separator which is a stabilizer for an associated valved stopper in a syringe barrel.

It is an object to provide an interface between a valved stopper and a separator such that displacement of the valved stopper likewise displaces the separator.

These and other objects and features of the present invention will be apparent from the detailed description taken with reference to accompanying drawings.

BRIEF DESCRIPTION OF THE DRAWINGS

FIG. 2 is a perspective of the two chamber mixing syringe assembly seen in FIG. 1 with a valved stopper disposed in a first state and displaced as fluid is drawn from a more distal chamber into a more proximal chamber for mixing.

FIG. 4 is a distal perspective of a valved stopper which separates the more distal chamber from the more proximal chamber in FIGS. 1 and 2.

FIG. 4A is a cross section of the valved stopper seen in FIG. 4 taken along lines 4A–4A.

FIG. 5 is a proximal perspective of the valved stopper seen in FIG. 4.

FIG. 6 is a distal perspective of the valved stopper seen in FIG. 4, with a slit valve disposed in a second or open state.

FIG. 6A is a distal perspective of a valve stopper similar to the valved stopper seen in FIG. 6, but with an open state which forms a one-way valve about a slit.

FIG. 7 is a distal perspective of a plunger which is associated with a stem of the syringe seen in FIGS. 1 and 2.

FIG. 8 is a perspective of the syringe assembly of FIGS. 1 and 2 with the valved stopper displaced to abut the most distal inner front surface of the syringe barrel.

FIG. 14 is an in-line perspective of the valved stopper, valve assembly and plunger seen in FIGS. 11 and 12.

FIG. 15 is a perspective the valve assembly seen in FIG. 14.

FIG. 16 is a perspective of the valved stopper and the valve assembly, each with a slit valve disposed to an open state.

FIG. 22 is a perspective of a two chamber mixing syringe assembly similar to the syringe assembly seen in FIGS. 1–8, but having a valved stopper molded with a dome inverted relative to the valved stopper seen in FIGS. 1–8.

FIG. 23 is a perspective of a syringe assembly similar to the syringe assembly seen in FIG. 22 with a valve of a valved stopper disposed in an open state, the valved stopper being displaced proximally relative to the valved stopper seen in FIG. 22.

FIG. 24 is a distal perspective of the valve stopper of the syringe assembly seen in FIGS. 22 and 23 which separates a more distal chamber from a more proximal chamber in FIG. 22.

FIG. 25 is a distal perspective of the valve stopper seen in FIGS. 22–24 with a valve of the valved stopper disposed in an open state.

DETAILED DESCRIPTION OF THE ILLUSTRATED EMBODIMENTS

In this description, primes of numbers are used to represent parts which are similar, but not identical to other parts having the same numbers. Reference is now made to embodiments illustrated in FIGS. 1–25 wherein like numerals are used to designate like parts throughout. Note that FIGS. 1–21 generally disclose elements associated with a first embodiment of the instant invention while FIGS. 22–25 disclose elements associated with a second embodiment of the instant invention.

Figure 1A:
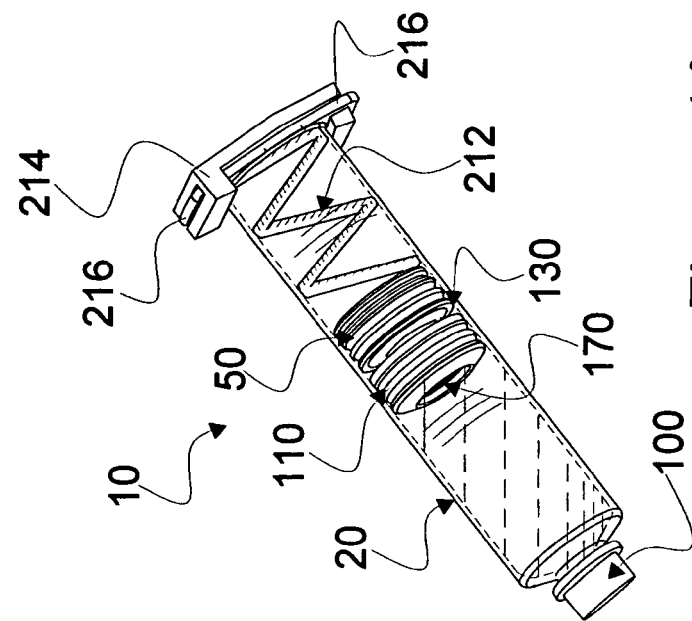
FIG. 1A is a perspective of the two chamber mixing syringe assembly seen in FIG. 1 with a syringe stem removed and replaced by a spring assembly which biases pressure against more distal parts to provide stability for the valve in the valved stopper in shipping, handling and storage prior to use.
Figure 1:
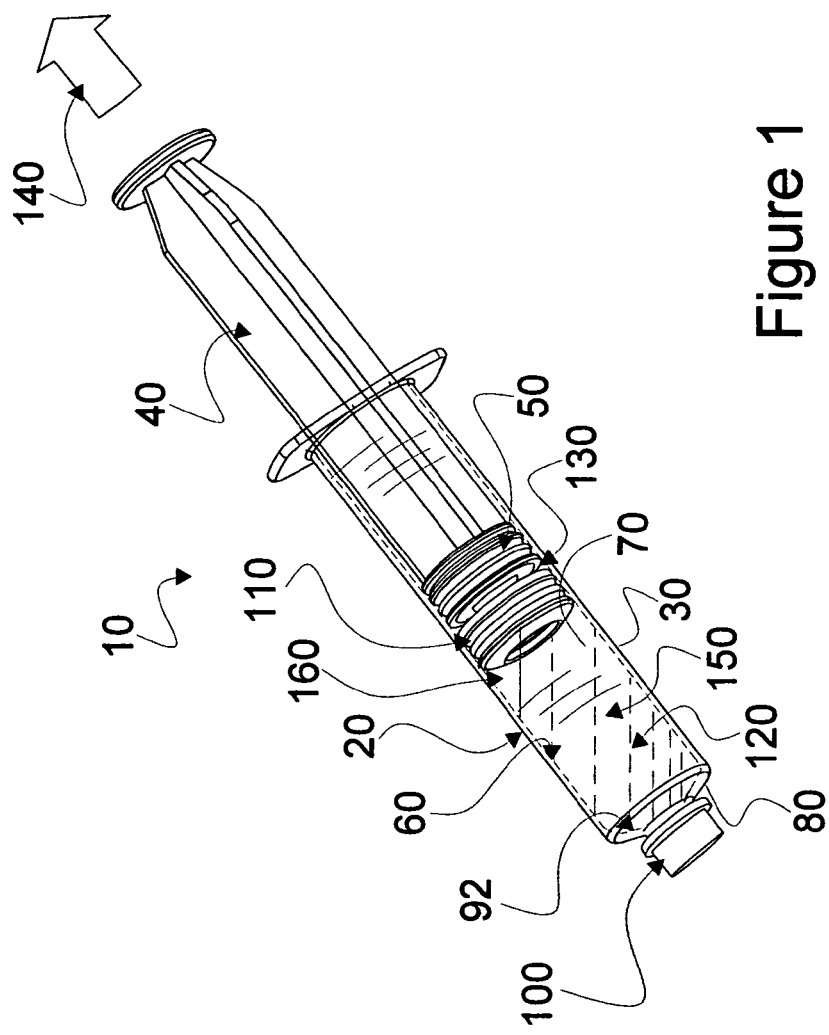
FIG. 1 is a perspective of a two chamber mixing syringe assembly made according to the instant invention, a syringe of the syringe assembly comprising a barrel having a traditional elongated substantially cylindrical shape.

Reference is now made to FIG. 1 wherein a two chamber mixing syringe assembly 10 made according to the instant invention is seen. Mixing syringe assembly 10 is assembled using a conventional syringe 20 which comprises a traditional elongated, cylindrical barrel 30, a stem 40 and a plunger 50 associated with stem 40.

Plunger 50, as is the case for most syringe plungers, is disposed within a hollow cylinder 60 of barrel 30 and is sufficiently close fitting to be fluid tight and wipe liquid from an inner surface 70 of cylinder 60 when displaced through barrel 30. Further, barrel 30 is closed at a distal end 80, except for a fluid dispensing orifice 90 (seen in FIGS. 9 and 10).

Note, that distal end 80 has an interior surface 92 which is contoured to maximize effluent flow and minimize dead space to thereby minimize fluid retained in barrel 30 as a plunger or stopper is displaced to abut distal end 80. During the mixing phase, orifice 90 is closed and sealed by a removable cap 100. Preferably, orifice 90 and cap 100 have associated luer and luer-lock fittings for fluid tight connection.

Disposed within barrel 30 between plunger 50 and interior surface 92 is a valved stopper 110. Valved stopper 110 divides space within barrel 30 into two chambers (i.e. distal chamber 120 and proximal chamber 130). Though proximal chamber 130 is seen to be much smaller in FIG. 1 than distal chamber 120, such is not necessarily always the case. The relative size of chamber 120 to chamber 130 may vary dependent upon concentrations and quantities of material to be mixed.

To mix fluids contained in chamber 120 with material contained in chamber 130, stem 40 (and plunger 50) are displaced in the direction of arrow 140. As may be noted in FIG. 1, contents of chamber 120 include a liquid 150 (usually a diluent) and a small amount of gas 160 (likely air and diluent vapor). Smaller chamber 130 may contain a lyophilized solid and gas or a fluid. Contents of chamber 130, either the lyophilized solid or a fluid, are destined to be diluted by liquid 150 from chamber 120. Gas 160 may be small in volume compared to liquid 150, but it is prudent to have that small elastic material volume in chamber 120 to facilitate creation of negative pressures in chamber 120 during the mixing process.

Reference is now made to FIG. 4 wherein a distal side 162 valved stopper 110 is seen. Though other kinds of valved bi-state stoppers may be employed within the scope of the instant invention, valved stopper 110 comprises a medially disposed dome 170 which has a concave surface 172, relative to distal side 162. Centrally disposed across dome 170 is a slit 180, which remains closed when a positive pressure gradient of a predetermined magnitude (measured from proximal side 182 to distal side 162) is imposed thereupon.

Dome 170 is better seen in FIG. 4A to comprise a convex proximal surface 184 juxtaposed concave surface 172. As seen in FIG. 5, proximal side 182 comprises a cylindrical inner surface 186 which forms a hollow well 188 leading to dome 170. Valved stopper 110 comprises a ribbed cylindrical exterior surface 190 which is sized and shaped to fit into barrel 30 and displace fluids within into barrel 30 in the same manner as plunger 50.

When a negative pressure gradient is imposed upon valved stopper 110, by displacing stem 40 in direction of arrow 140 (see FIG. 1), that negative pressure is also disposed across dome 170. Under such conditions, dome 170 "balloons" and slit 180 opens to permit a portion of the fluid (liquid 150 and gas 160) disposed in chamber 120 to pass into chamber 130. When the displacing force is removed from stem 40, equilibrating forces of ambient air and previously internally generated negative pressures displace plunger 50 distally to the position from which it was earlier displaced and, because slit 180 closes when equilibrating forces impose a positive pressure gradient across valved stopper 110, stiction and friction are overcome to displace valved stopper 110, distally, as seen in FIG. 2.

Successive proximal displacements of stem 40 result in additional flow of fluid from chamber 120 into chamber 130. Each subsequent release of force from stem 40 results in distal displacement of valved stopper 110. Ultimately, substantially all of the fluid originally disposed in chamber 120 is displaced into chamber 130 to mix with the contents thereof. At this point, valved stopper 110 abuts distal interior surface 92, as seen in FIG. 8. Preferably, distal face 162 of valved stopper 110 is contoured to minimize dead space and, thereby, maximize mixing of contents of chambers 120 and 130.

Figure 3:
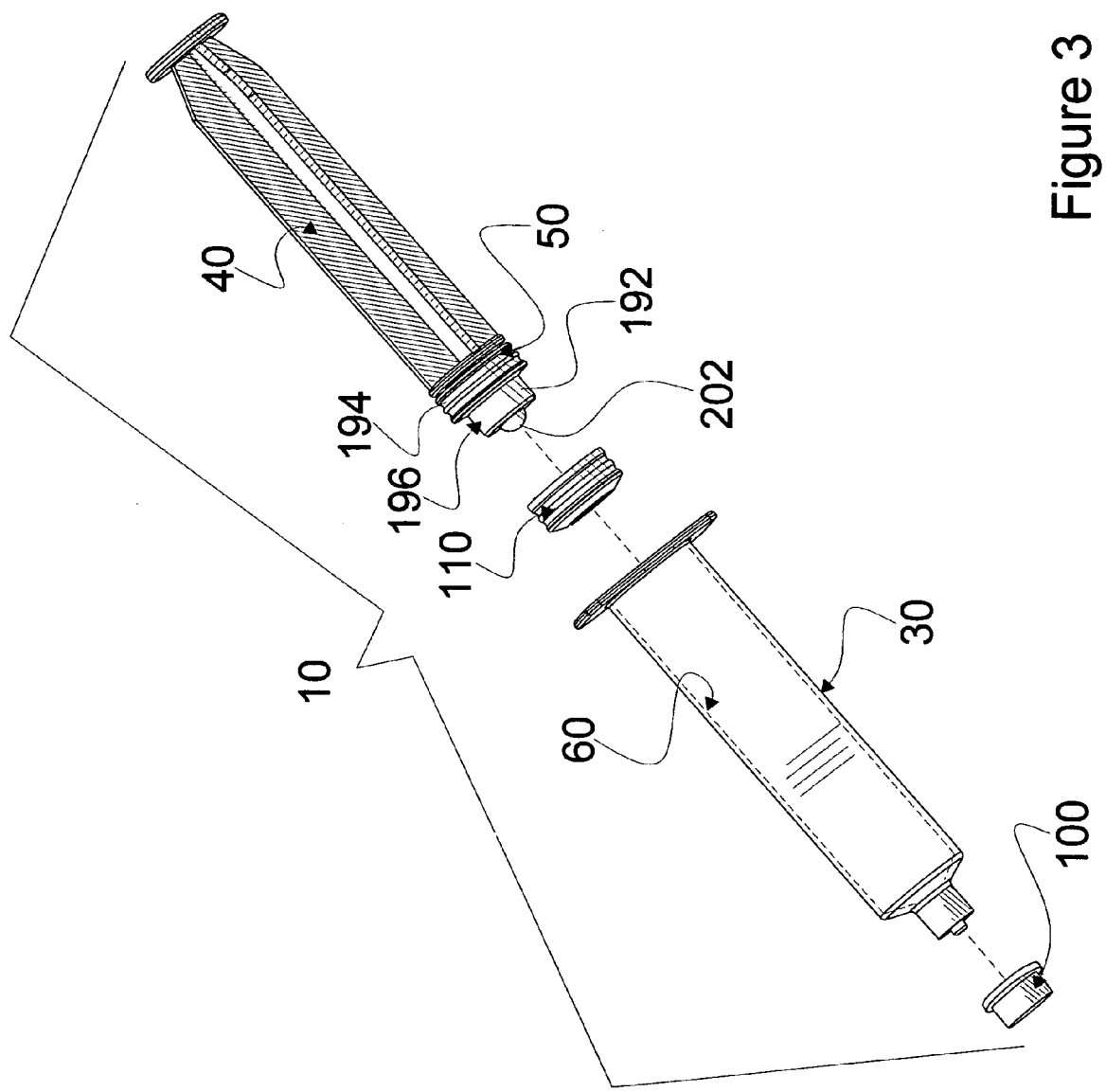
FIG. 3 is an exploded view of the two chamber mixing syringe assembly seen in FIGS. 1 and 2.

Form and shape of discreet parts of mixing syringe assembly 10 are seen in FIG. 3. Cap 100 is securely but releasibly affixable to syringe barrel 30. Syringe barrel 30 is the form of a cylinder (hollow cylinder 60) of substantially constant diameter. Valved stopper 110 fits into barrel 30 in a manner similar to the way plunger 50 fits into barrel 30. Plunger 50 is either affixed to stem 40 prior to insertion of plunger 50 into barrel 30 or is attached just before use as is disclosed hereafter. Special attention should be made to form of a distal portion 192 of plunger 50, which is better seen in FIG. 7.

As earlier mentioned, plunger 50 has a cylindrical ribbed exterior surface (numbered 194 in FIGS. 3 and 7) which provides a fluid tight interface with interior barrel surface 60. Distal from surface 194, portion 192 comprises a solid cylindrical section 196 which is sized and shaped to nest within well 188 (see FIG. 5). Also portion 192 abruptly ends in a distal front face 198 which is shaped and contoured to fit against a proximal face portion 200 of well 188 of which stopper 110 (again, see FIG. 5) to thereby dispense any remaining fluid from well 188 when portion 192 is completely nested therein.

As is disclosed in detail hereafter, dome 170 inverts under force of a predetermined positive pressure gradient to an inverted or switched state as seen by examples of domes 170 and 170' in FIGS. 6 and 6A. For this reason, portion 192 has a nose section 202 (again see FIG. 7) seen to be medially, distally protruding out of face portion 200. Portion 200 is sized and shaped to fit within a hollow formed by inverting dome 170 or 170' to thereby expel remaining fluid therefrom when portion 192 is completely nested therein.

When valved stoper 110 is displaced to abut distal end 92 as seen in FIG. 8, dome 170 and slit 180 are initially disposed as seen in FIGS. 4 and 4A. A predetermined positive pressure gradient disposed across valved stopper 110, when valved stopper 110 is abutting distal end 92, displaces or switches dome 170 to a second state (seen in FIGS. 6 and 6A). Most commonly, cap 100 is removed from syringe 20 before applying a force upon stem 40 which provides the pressure gradient to switch either dome 170 or 170'.

Figure 9:
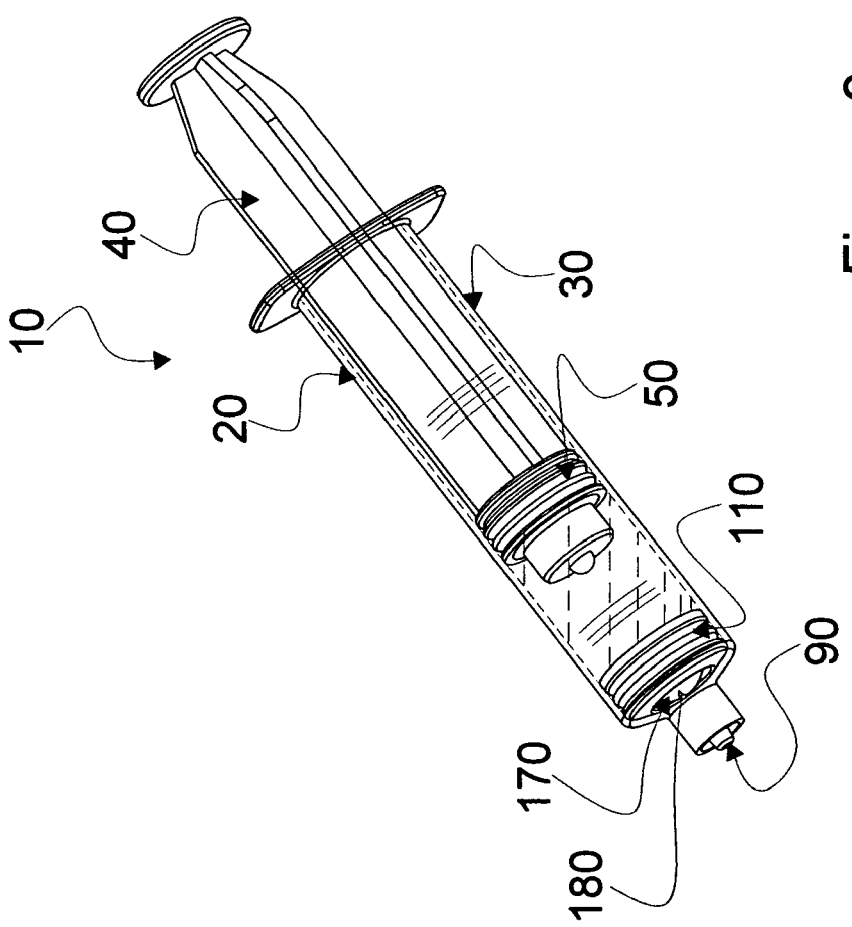
FIG. 9 is a perspective of the syringe assembly of FIG. 8 with a cap removed and the valve of the valved stopper disposed in an open state such that fluid may be dispensed from the syringe barrel.

Once mixing is considered complete, cap 100 is removed preparatory to dispensing fluid from barrel 30. As seen in FIG. 9, force is applied to switch dome 170 to open slit 180 when a positive pressure is applied (in direction of arrow 210) and fluid is dispensed from syringe 20 as seen in successive steps in FIGS. 9 and 10 (in the same manner as fluid is dispensed from a conventional, single-chamber syringe. Note, in FIG. 10 that plunger 50 is well nested into valved stopper 110 to assure substantially all fluid has been eliminated from syringe 20.

In some cases, however, there may be fluids, disposed within chamber 130 after completing an initial mixing step, for which additional agitated mixing is desired. In this case, design of a dome, such as dome 170' seen in FIG. 6A, may be used. Dome 170' has a thinned area 204 disposed about a slit 180'. When dome 170' is switched, material of thinned area 204 collapses to form a "duck-bill" like valve 206. So formed, valve 206 opens to a positive pressure gradient across associated valved assembly 110 and closes when an imposed pressure gradient is either negative or zero.

Figure 8A:
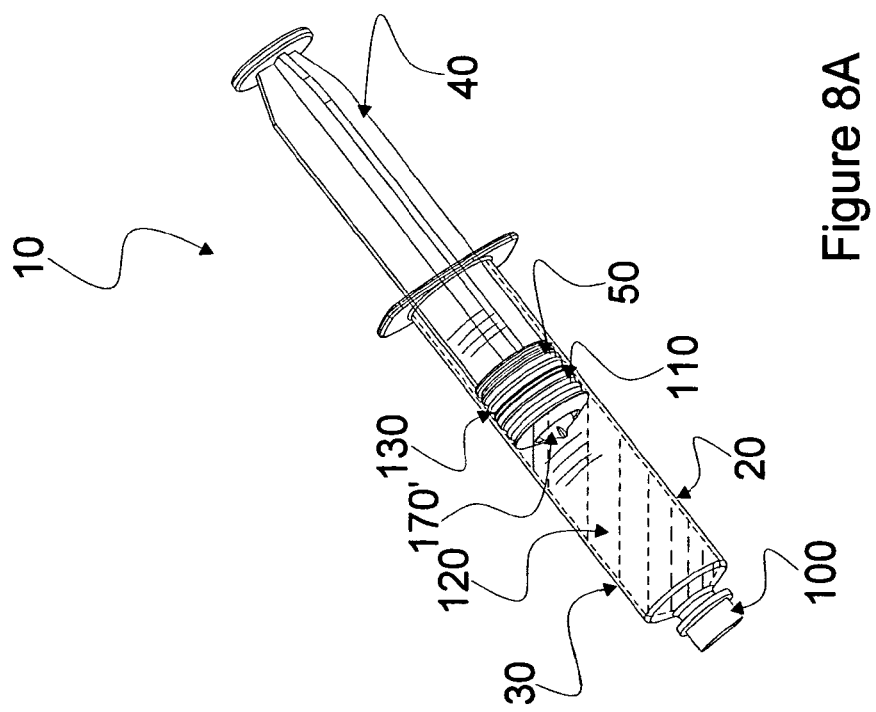
FIG. 8A is a perspective of a syringe assembly similar to the syringe assembly seen in FIG. 8 with a valve of a valved stopper switched to an open state, the valved stopper displaced proximally relative to the valved stopper seen in FIG. 8.
Figure 10:
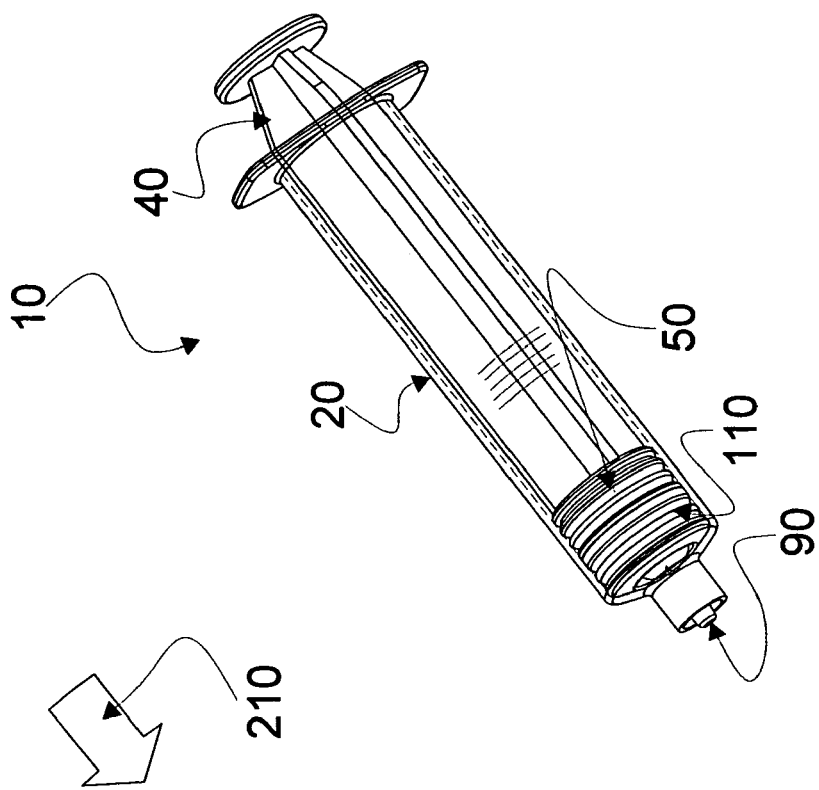
FIG. 10 is a perspective of the syringe assembly of FIGS. 7 and 9 with fluid completely dispensed and the plunger nested into the valved stopper to minimize dead space.

Thus, imposing a positive force on stem 40 in the direction of arrow 210, when valved stopper is disposed as seen in FIG. 8, forces a change in dome 170' to the state seen in FIG. 6A. Continuing force in the same direction drives fluid from chamber 130 back into chamber 120. By applying successive iterations of such force upon stem 40, substantially all fluid is pumped out of chamber 130 into chamber 120 as seen in FIG. 8A.

As disclosed supra, once mixing is complete, cap 100 is removed and fluid is dispensed in the same manner as with a conventional, single-chamber, syringe. While, in the case of a dome 170', valved stopper 110 and plunger 50 are already nested and operate as a single plunger part to dispense fluid from chamber 120. In the case of dome 170 (see FIG. 9), plunger 50 is distally displaced in direction of arrow 210 to dispense mixed fluid through valved stopper 110.

Reference is now made to FIG. 1A wherein stem 40 (see FIG. 1) is removed from plunger 50. In place of stem 40, a biasing memory element (e.g. in the form of spring 212) produces a biasing force and resulting positive pressure gradient across valved stopper 110 and associated dome 170 (see FIG. 4A). Spring 212 is kept in place by a clip 214 affixed in bayonet fashion to flanges 216 of syringe barrel 20. So disposed, spring 212 maintains sufficient pressure across dome 170 to keep slit 180 closed under shipping, storage and other conditions prior to use. To use syinge assembly 10, clip 214 and spring 212 are removed before use and stem 40 is affixed to plunger 50. Such stem and plunger attachments are well known in the syringe art.

Figure 11:
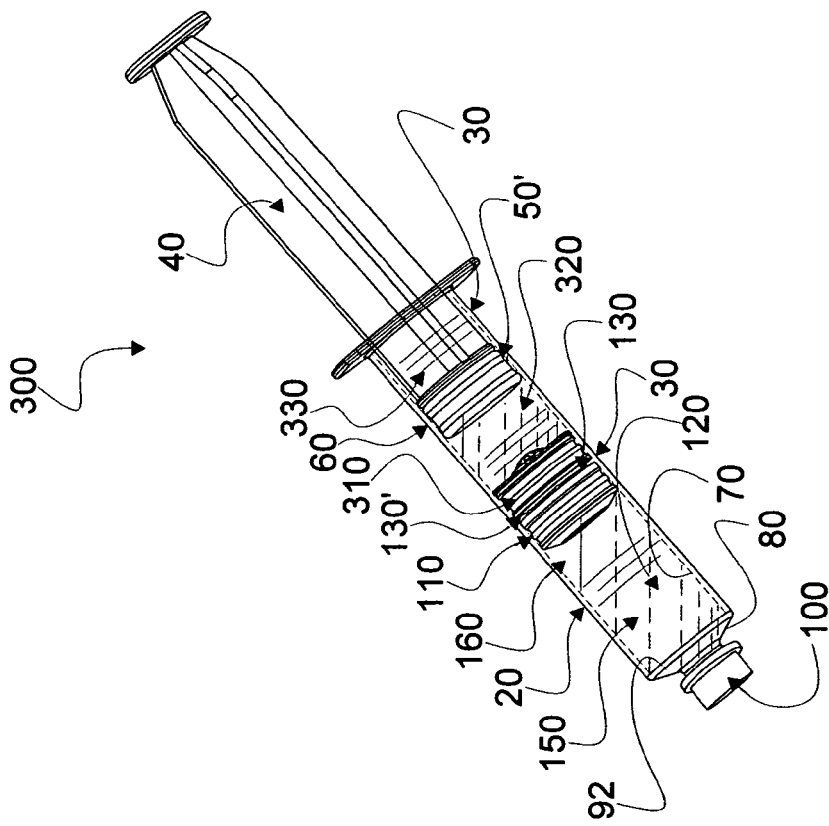
FIG. 11 is a perspective of a three chamber mixing and flush syringe assembly according to the invention which is similar to the syringe assembly seen in FIG. 1, but having a valve assembly which separates the more proximal chamber of the syringe of FIG. 1 into a middle chamber and a most proximal chamber.

Reference is now made to FIG. 11 wherein a three chamber, combination mixing and flushing syringe assembly 300 is seen. The combination forming syringe assembly 300 is assembled using a conventional syringe 20 which comprises a traditional elongated, cylindrical barrel 30, a stem 40 and a plunger 50' associated with stem 40.

As disclosed supra, plunger 50', as is the case for most syringe plungers, is disposed within a hollow cylinder 60 of barrel 30 and is sufficiently close fitting to be fluid tight and wipe liquid from inner surface 70 of cylinder 60 when displaced through barrel 30. Further, barrel 30 is closed at a distal end 80, except for a fluid dispensing orifice 90 (seen in FIGS. 13 and 19–21).

Note, that distal end 80 has an interior surface 92 which is contoured to maximize effluent flow and minimize dead space to thereby minimize fluid retained in barrel 30 as a plunger (when there is no intermediate valved stoppers) is displaced to abut distal end 80. During the mixing phase, orifice 90 is closed and sealed by removable cap 100. Preferably, orifice 90 and cap 100 have associated luer and luer-lock fittings for fluid tight connection, as anticipated supra.

Disposed within barrel 30 between plunger 50' and interior surface 92 is a valved stopper 110. As disclosed supra, valved stopper 110 divides space within barrel 30 into two chambers (i.e. chamber 120 and chamber 130). Chamber 130 is further divided, by a valve assembly 310, into a middle chamber 130' and a most proximal chamber 320. As related supra, although a chamber proximally disposed relative to chamber 120, such as chamber 130', is seen to be much smaller in FIG. 11 than chamber 120, such is not necessarily always the case. The relative size of chamber 120 to chamber 130' may vary dependent upon concentrations and volumes of solutions to be mixed.

To mix fluids contained in chamber 120 with fluids contained in chamber 130', stem 40 (and plunger 50' and valve assembly 310) are displaced in the direction of arrow 140. As may be noted in FIG. 11, contents of chamber 120 include a liquid 150 (usually a diluent) and a necessary small amount of gas 160 (likely air and diluent vapor). Smaller chamber 130' may contain a lyophilized solid and gas or a fluid. Each of the lyophilized solid or the fluid is destined to be diluted by liquid 150 from chamber 120. Gas 160 may be small in volume compared to liquid 150, but it is prudent to have that small volume to facilitate creation of negative pressures in chamber 120 during the mixing process.

It is important to note that valve assembly 310 operates in a manner identical to a valve assembly disclosed in Thorne, Jr. (referenced as valve assembly 550, therein). Valve assembly 550 is assembled using a valved stopper 580 and a separator 700, as numbered in Thorne, Jr. As disclosed in Thorne, Jr., a flush syringe employing valve assembly 550 may be used in a manner identical to a standard or conventional syringe. For this reason, valve assembly 310 and fluid content 330 in most proximal chamber 320 may, operationally relative to displacement of valved stopper 110, be considered to be a mechanical extension of plunger 50'. Therefore, all disclosure relative to mixing of contents of chambers 130 and 120 for syringe assembly 10 is relevant and the same as that for syringe assembly 300 and associated chambers 130' and 120.

Note, as seen in FIGS. 14–16, valve assembly 310 is assembled using a valved stopper 340 and a separator 370. A singular difference between valved stopper 340 and valved stopper 580 as disclosed in Thorne, Jr. is an elongated front section 350 of valved stopper 340 as seen in FIGS. 14–16. Front section 350 is sized and shaped to nest within well 188 (see FIGS. 4A and 5) as portion 192 of plunger 50 so nests in syringe assembly 10 (see FIGS. 8A and 10). However, valved stopper 340 comprises a bi-stable slit valve 376 having a dome 374 which inverts when switched (see FIG. 14 prior to switching and FIG. 16 after switching). Note also, that a switched dome 374 provides a bulbous protrusion of front section 350 which expels fluid from well 188, in the same manner that nose section 202 does for plunger 50. Gas separator 370 is functionally identical to separator 700 of Thorne, Jr. Plunger 50' preferably has a flat or planar distal face 380.

Figure 12:
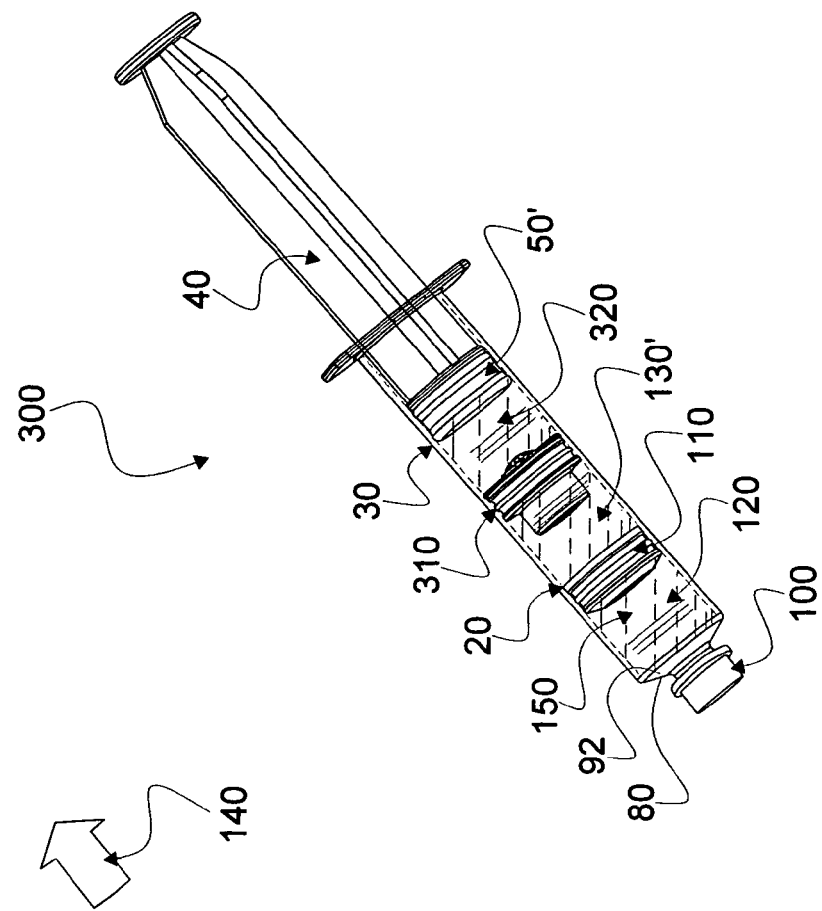
FIG. 12 is a perspective of the three chamber mixing and flush syringe assembly seen in FIG. 11, but with the valve assembly displaced away from the valved stopper to provide a larger middle chamber than is seen in the middle chamber of FIG. 11.
Figure 13:
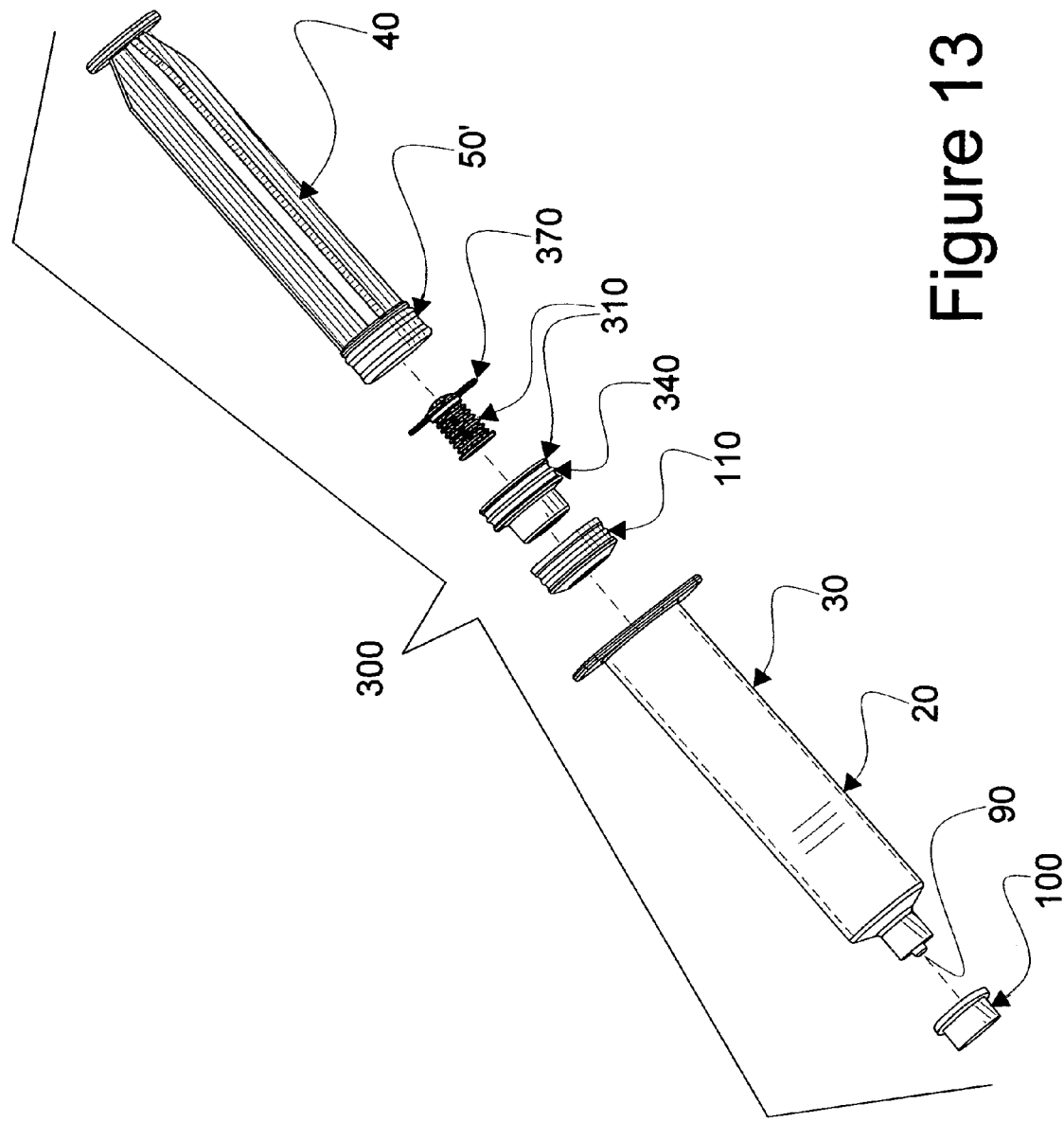
FIG. 13 is an exploded view of the three chamber mixing and flush syringe assembly seen in FIGS. 11 and 12.
Figure 21:
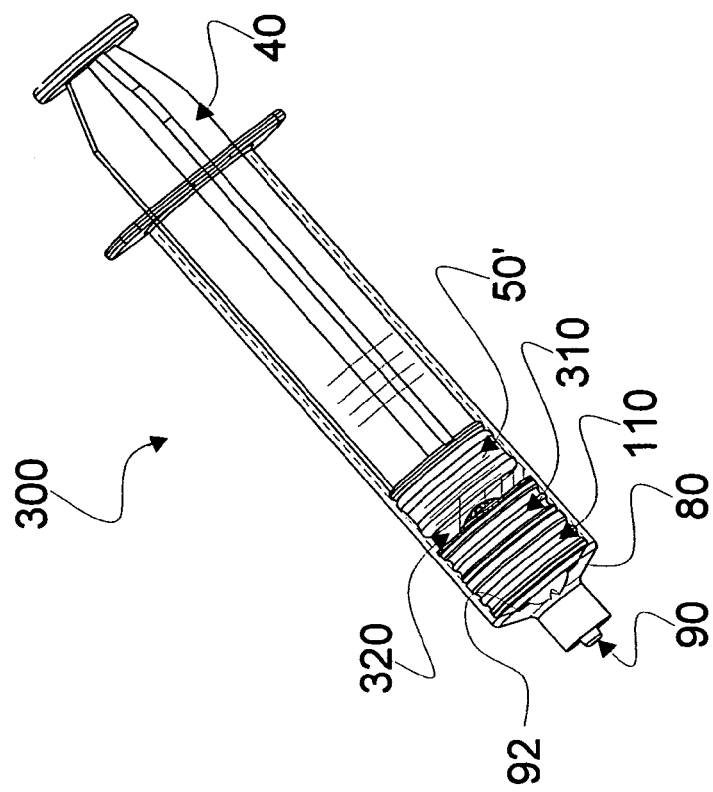
FIG. 21 is a perspective of the three chamber mixing and flush syringe assembly, seen in FIG. 20, with fluid from the most proximal chamber dispensed, but with the plunger retained at a non-abutting distance from the valve assembly to guard against reflux.
Figure 20:
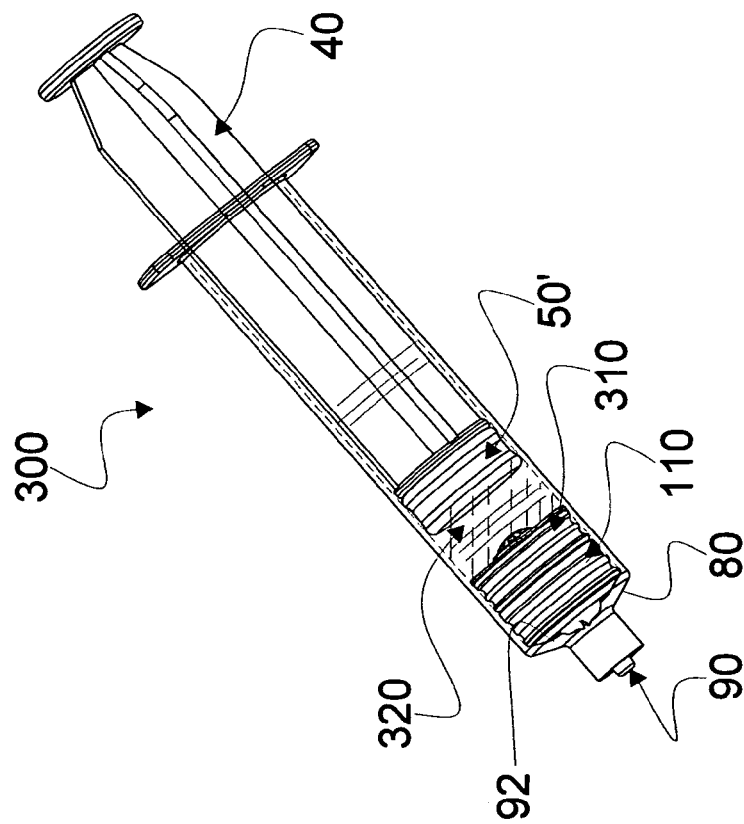
FIG. 20 is a perspective of the three chamber mixing and flush syringe assembly, seen in FIGS. 18 and 19, with the valve assembly nested into recesses of the valved stopper and with both valves open to permit dispensing of a flush from the most proximal chamber the barrel.

Order of assembly of parts to make mixing syringe assembly 300 is seen in FIG. 13. Valved stopper 110 is displaced into barrel 30 to close most distal chamber 120, followed by insertion of valve assembly 310 (made from valved stopper 340 and separator 370) to form middle chamber 130' and, finally, insertion of plunger 50' to close most proximal chamber 320. Chambers 120, 130' and 320 are seen in FIG. 12. Separator 370 is seen assembled into valved stopper 340 in FIG. 15. Valved stoppers 110 and 340 are seen in FIG. 16 with domes 170 and 374 inverted to a second state with slits 180 and 376 open. Such is the case, when liquid is being dispensed from chamber 320 as seen in FIGS. 20 and 21 and disclosed in more detail hereafter.

Figure 17:
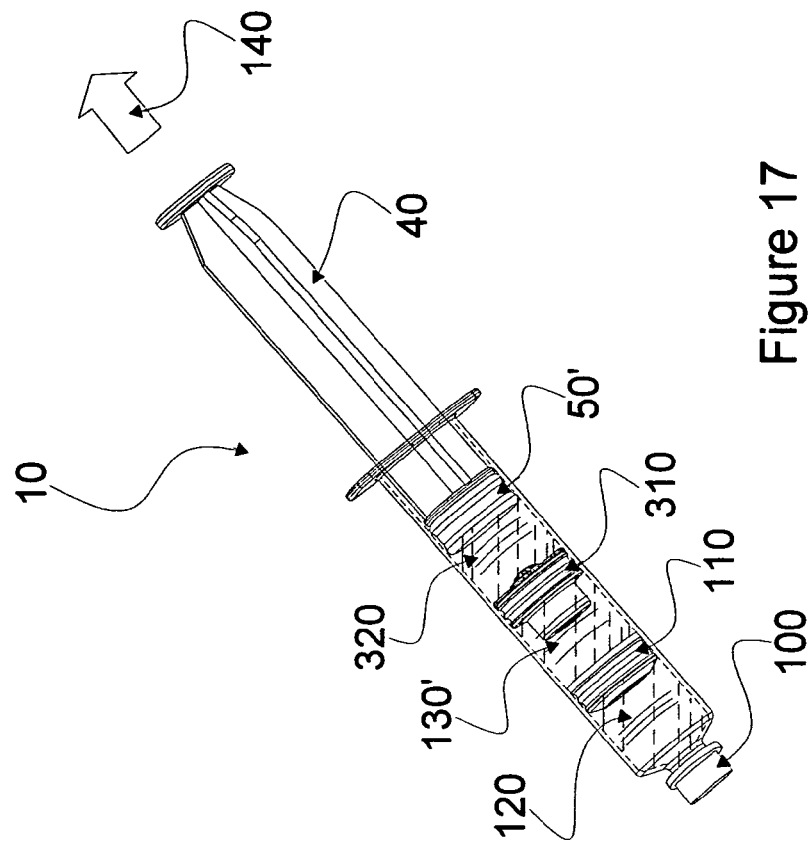
FIG. 17 is a perspective of the three chamber mixing and flush syringe assembly seen in FIG. 11 with a portion of the fluid earlier disposed in the distal chamber drawn into the middle chamber.

Reference is now made to FIG. 17 wherein volume of fluid in middle chamber 130' is seen to be increased from volume of material in chamber 130' in FIG. 11 by successive pulls in direction of arrow 140 of stem 40. Note that volume of chamber 320 in FIG. 17 is substantially the same as volume of chamber 320 in FIG. 11. This is because there is no material change in chamber 320 resulting from success pulls on stem 40.

Figure 19:
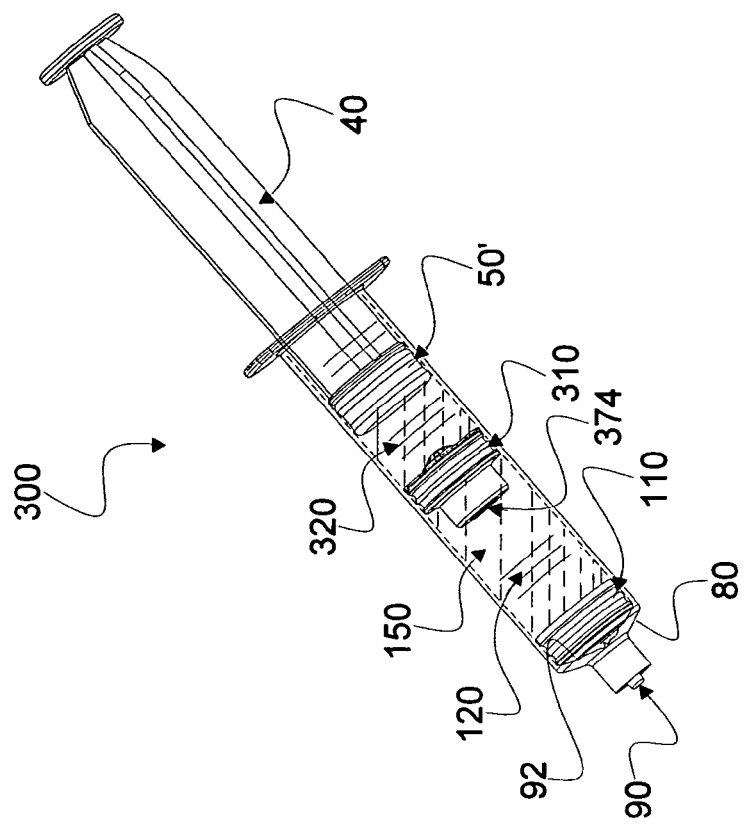
FIG. 19 is a perspective of the three chamber mixing and flush syringe assembly seen in FIG. 18, but with a cap removed and valve of the valved stopper open for dispensing fluid from the syringe barrel.
Figure 18:
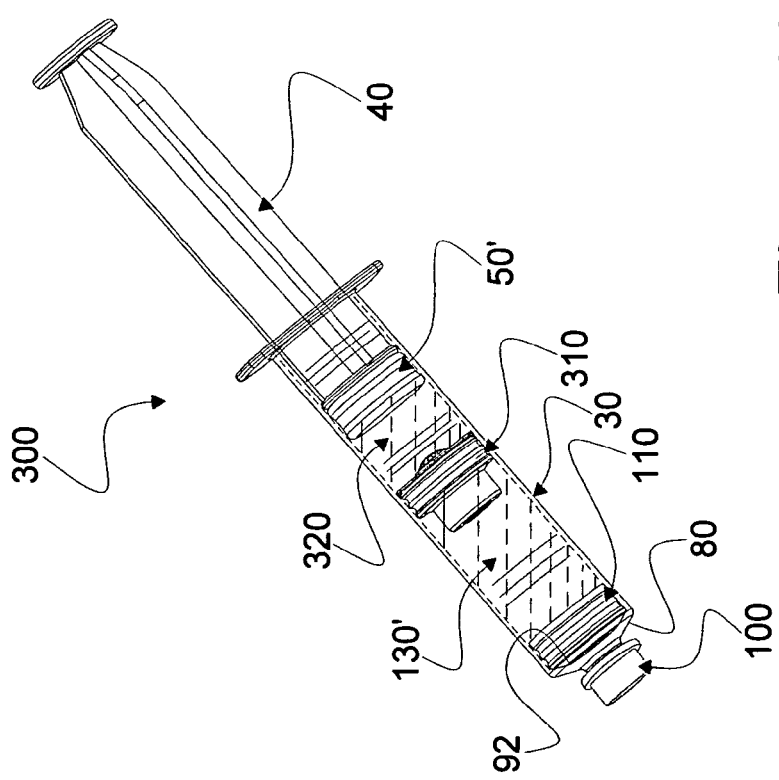
FIG. 18 is a perspective of the three chamber mixing and flush syringe assembly seen in FIG. 17 with the valved stopper displaced to abut the inner distal surface of the syringe barrel.

Ultimately, as seen in FIG. 18, valved stopper 110 is displaced, by successive pulls on stem 40, to abut distal end 80 of syringe barrel 30. At this point, when mixing is considered complete, cap 100 is removed, as seen in FIG. 19. Forcing stem 40 distally, first dispenses fluid from chamber 120 after inverting dome 170 and opening slit 180. After chamber 120 is emptied, dome 374 is inverted (see FIG. 16) and slit 376 is opened to permit emptying of chamber 320 as seen in FIG. 20. Finally, substantially all fluid desired to be effluent is dispensed as seen in FIG. 21. Note, that plunger 50' is not in contact with valve assembly 310 at the end of the dispensing cycle. Such is preferred to eliminate the possibility of reflux.

An alternate embodiment of a mixing syringe assembly 400 is seen in FIGS. 22–25. In this embodiment, a material to be mixed or diluted is initially disposed in a distal chamber 120. A diluent is disposed in a more proximal chamber 130, just opposite of the material/diluent disposition of FIGS. 1–21. However, it is emphasized that mixing dispositions and methods disclosed for this embodiment are applicable to associated dispositions and methods disclosed for syringe assemblies 10 and 10', supra. A simple change in geometry or operation in a valved stopper provides for changes in operative procedures disclosed hereafter.

Reference is now made to FIG. 22 wherein a mixing syringe assembly 400 is seen. In FIG. 22, a material to be diluted is disposed in chamber 120 between a valved stopper 170" and interior surface 92 of distal end 80 of syringe 20. A diluent is disposed in chamber 130 between valved stopper 170" and a plunger 50. It is important to note that plunger 50 and valved stopper 170" have the same nesting characteristics as disclosed supra for plunger 50 and stopper 110.

As disclosed supra, distal end 80 of syringe 20 has an interior surface 92 which is contoured to maximize effluent flow and minimize dead space to thereby minimize fluid retained in barrel 30 as a plunger or stopper is displaced to abut distal end 80. During the mixing phase, orifice 90 is closed and sealed by a removable cap 100. Preferably, orifice 90 and cap 100 have associated luer and luer-lock fittings for fluid tight connection.

Disposed within barrel 30 between plunger 50 and interior surface 60 is a valved stopper 110'. Valved stopper 110' divides space within barrel 30 into two chambers (i.e. distal chamber 120 and proximal chamber 130). In this embodiment, chamber 120 is seen to be much smaller in FIG. 22 than distal chamber 130, as the diluent is anticipated to be stored in chamber 130. Such is not necessarily always the case. The relative size of chamber 130 to chamber 120 may vary dependent upon concentrations and quantities of material to be mixed.

To mix fluids contained in chamber 130 with material contained in chamber 120, stem 40 (and plunger 50) are displaced in the direction of arrow 210. As may be noted in FIG. 22, contents of chamber 130 include a liquid 150 (usually a diluent) and a small amount of gas 160 (likely air and diluent vapor). Smaller chamber 120 may contain a lyophilized solid and a necessary volume of gas 402 or a fluid and gas 402. Contents of chamber 120, either the lyophilized solid or a fluid, are destined to be diluted by liquid 150 from chamber 130. Gas 402 may be small in volume compared to other contents of chamber 120, but it is prudent to have that small elastic material volume in chamber 120 to facilitate the mixing process.

Reference is now made to FIG. 24 wherein a distal side 162' valved stopper 110' is seen. Though other kinds of normally-closed valved stoppers may be employed within the scope of the instant invention, valved stopper 110' comprises a medially disposed dome 170" which has a convex surface 172', relative to distal side 162'. Centrally disposed across dome 170" is a slit 180', which remains closed when a negative or zero pressure gradient (measured from proximal side 182' to distal side 162') is imposed thereupon.

Generally, other than dome 170", valved stopper 110' has the same physical dimensions and characteristics as those of valved stopper 110. When a positive pressure gradient is imposed upon valved stopper 110', by displacing stem 40 in direction of arrow 210 (see FIG. 22) that negative pressure is also disposed across dome 170". Under such conditions, dome 170" "balloons" and slit 180' opens to permit a portion of the fluid (liquid 150 and gas 160) disposed in chamber 130 to pass into chamber 120. When the displacing force is removed from stem 40, equilibrating forces of ambient air and previously internally generated pressures displace plunger 50 proximally to the position from which it was earlier displaced and, because slit 180' closes when equilibrating forces impose a negative pressure gradient across valved stopper 110', stiction and friction are overcome to displace valved stopper 110', proximally.

Successive distal displacements of stem 40 result in additional flow of fluid from chamber 130 into chamber 120. Each subsequent release of force from stem 40 results in proximal displacement of valved stopper 110'. Ultimately, substantially all of the fluid originally disposed in chamber 130 is displaced into chamber 120 to mix with the contents thereof. At this point, valved stopper 110' abuts plunger 50, as seen in FIG. 23.

Once all fluid is emptied from chamber 130 into chamber 120 and mixing is complete, cap 100 is removed. Interestingly, there is no need for the valve, associated with dome 170", to be switched to a second state, other than an open state in this embodiment, to dispense fluids from syringe 20. Interestingly, once mixing has completed in syringe assembly 400, there is substantially no fluid yet to be displaced through valved stopper 110', as valved stopper 110' is then displaced to abut plunger 50. Therefore, cap 100 simply has to be removed and stem 40 and plunger 50 displaced distally to dispense mixed fluid from mixing syringe assembly 400. Also a negative pressure bias is best used to keep material in chambers 120 and 130 disparate during shipping, handling and otherwise before use.

The inventions disclosed herein may be embodied in other specific forms without departing from the spirit or essential characteristics thereof. The present embodiments are therefore to be considered in all respects as illustrative and not restrictive, the scope of these inventions being indicated by the appended claims rather than by the foregoing description, and all changes which come within the meaning and range of equivalency of the claims are therefore intended to be embraced therein.

What is claimed and desired to be secured by Letters Patent is:

1. A mixing syringe apparatus for mixing and dispensing medical fluids, said apparatus comprising:

a syringe comprising a conventional hollow barrel having an elongated internal cylindrical surface, said barrel surface comprising an open proximal end and a distal end having a closed interior about an orifice through which fluid is transferred, and a stem and plunger combination, said combination being disposed to be displaced within said barrel by application of force in a predetermined direction against said stem thereby imposing predetermined differential pressures for displacing fluid within the barrel; and a removable cap which, in combination with said plunger, fully confines all fluid and material previously stored within said syringe barrel between the plunger and cap;

a displaceable valved stopper disposed within said barrel between said plunger and said distal end to provide a more proximal chamber disposed between the plunger and valved stopper as a container for a first volume of matter and a more distal chamber disposed between the distal end and valved stopper as a container for a second volume of matter, said first and second volumes of matter being kept disparate before mixing and mixed by action of force directed in the predetermined direction upon the stem of the syringe;

said displaceable valved stopper comprising a normally-closed valve which yields to an open state when the predetermined pressure differential is disposed across the valved stopper, the pressure differential causing diluting matter in a fluid state to be dispensed through the valve, thereby to mix the diluting fluid from the dispensing chamber with matter resident in the receiving chamber;

an elastic fluid disposed within the more distal chamber for storing energy resulting from pressure derived from force applied in the predtermined direction upon the stem of the syringe, at least a portion of the stored energy effecting displacement of the valved stopper in a direction opposite direction of the applied predetermined force, once that force is terminated, thereby changing size of one chamber relative to the other chamber and providing opportunity for additional dispensing of fluid through the valve by subsequent application of force in the predetermined direction.

2. A mixing syringe apparatus according to claim 1, wherein said valve comprises structure for permitting the valve to operate in two different states wherein the valve is patent to flow in one direction in one state and patent to flow an opposite direction in the other state.

3. A mixing syringe apparatus according to claim 1, wherein said valve comprises a non-planar structure.

4. A mixing syringe apparatus according to claim 3, wherein said non-planar structure is a dome structure.

5. A mixing syringe apparatus according to claim 3, wherein said non-planar structure comprises a valve formed by a slit.

6. A mixing syringe apparatus according to claim 1 wherein said apparatus further comprises a biasing memory element disposed in place of the stem within the barrel of the syringe for the purpose of maintaining a differential pressure across the valved stopper to keep the valve closed during shipping, storage and before use.

7. A mixing syringe apparatus according to claim 1 further comprising a valve assembly disposed within the more proximal chamber to provide a middle chamber for the medical material and a most proximal chamber for a disparate solution which is delivered separately from mixed matter and diluting fluid.

8. A mixing syringe apparatus for mixing and dispensing medical fluids, said apparatus comprising:
   a syringe comprising a conventional hollow barrel having an elongated internal cylindrical surface, said barrel surface comprising an open proximal end and a distal end having a closed interior about an orifice through which fluid is transferred, and a stem and plunger combination, said combination being disposed to be displaced within said barrel by application of force against said stem thereby imposing differential pressures for displacing fluid within the barrel; and
   a removable cap which, in combination with said plunger, fully confines all fluid and material previously stored within said syringe barrel between the plunger and cap;
   a displaceable valved stopper disposed within said barrel between said plunger and said distal end to provide a more proximal chamber disposed between the plunger and valved stopper as a container for a medical material and a more distal chamber disposed between the distal end and valved stopper as a container for a diluting fluid which is to be mixed with the first medical material;
   said displaceable valved stopper comprising;
      a switchable bi-state valve comprising two operating states, a first state in which said valve is closed to fluid flow when disposed away from said distal end and imposed upon by a non-negative differential pressure but which is permissive to proximally directed fluid flow when imposed upon by a negative differential pressure and a second state in which said valve is permissive to distally directed flow resulting from a positive pressure gradient, said valve further comprising switchable construction which is displaced to a second state upon application of a predetermined positive differential pressure across the valved stopper.

9. A mixing syringe apparatus according to claim 8, wherein said bi-state valve comprises a non-planar structure.

10. A mixing syringe apparatus according to claim 9, wherein said non-planar structure is a dome structure.

11. A mixing syringe apparatus according to claim 9, wherein said non-planar structure comprises a valve formed by a slit.

12. A mixing syringe apparatus according to claim 8 wherein said apparatus further comprises a biasing memory element disposed in place of the stem within the barrel of the syringe for the purpose of maintaining a positive differential pressure across the first valved stopper to keep the valve closed during shipping, storage and before use.

13. A mixing syringe apparatus according to claim 8 further comprising a valve assembly disposed within the more proximal chamber to provide a middle chamber for the medical material and a most proximal chamber for a disparate solution which is delivered separately from mixed medical material and diluting fluid.

14. A mixing syringe apparatus according to claim 13 wherein said valve assembly comprises a second valved stopper and a gas separator.

15. A method for using a mixing syringe apparatus for mixing and dispensing medical fluids comprising the following steps:
   (a) providing a syringe comprising a conventional hollow barrel having an elongated internal cylindrical surface, said barrel surface comprising an open proximal end and a distal end having a closed interior about an orifice through which fluid is transferred, and a stem and plunger combination, said combination being disposed to be displaced within said barrel by application of force against said stem thereby imposing differential pressures for displacing fluid within the barrel;
   (b) providing a removable cap which, in combination with said plunger, fully confines all fluid and material previously stored within said syringe barrel between the plunger and cap;
   (c) providing a displaceable valved stopper disposed within said barrel between said plunger and said distal end to provide a more proximal chamber disposed between the plunger and valved stopper as a container for a medical material and a more distal chamber disposed between the distal end and valved stopper as a container for a diluting fluid which is to be mixed with the first medical material;
   said displaceable valved stopper comprising;
      a switchable bi-state valve comprising two operating states, a first state in which said valve is closed to fluid flow when disposed away from said distal end and imposed upon by a non-negative differential pressure but which is permissive to proximally directed fluid flow when imposed upon by a negative differential pressure and a second state in which said valve is permissive to distally directed flow resulting from a positive pressure gradient, said valve further comprising switchable construction which is displaced to a second state upon application of a predetermined positive differential pressure across the valved stopper;
   (d) placing a force on said stem to displace said stem and plunger proximally from an original site relative to said barrel thereby opening the valve of the valved stopper and displacing a portion of the fluid in the more distal chamber into the more proximal chamber;
   (e) releasing the force from the stem, thereby permitting the valve to close, the stem and plunger to be displaced to the original site and the valved stopper to be distally displaced;
   (f) repeating steps (d) and (e) until substantially all of the fluid originally resident in the more distal chamber is displaced from the more distal chamber to mix with material in the more proximal chamber and the valved stopper is displaced to the distal end of the barrel surface.

16. The method for using a mixing syringe apparatus for mixing and dispensing medical fluids according to claim 15 comprising a further step of removing the cap from the syringe.

17. The method for using a mixing syringe apparatus for mixing and dispensing medical fluids according to claim 15 comprising a further step of applying a distally directed force upon the stem to exert a positive differential pressure across the valved stopper to switch the valve to the second state.

18. The method for using a mixing syringe apparatus for mixing and dispensing medical fluids according to claim 17 comprising a further step of continuing to apply distally directed force upon the stem to dispense fluid from the syringe.

19. The method for using a mixing syringe apparatus for mixing and dispensing medical fluids according to claim 15 comprising a further step of applying distally directed force upon the stem to switch the valve to the second state.

20. A method for using a mixing syringe apparatus for mixing and dispensing medical fluids according to claim 18 comprising a further steps of:

(g) continuing to apply distally directed force upon the stem to thereby open the valve and displace a portion of the mixed fluid in the more proximal chamber into the more distal chamber as the stem is displaced from an original site to a more distal site and (h) removing distally directed force from the stem and permitting valve to close and the stem and plunger to be displaced by stored pressure gradients instituted by the distally directed force to the original site.

21. The method for using a mixing syringe apparatus for mixing and dispensing medical fluids according to claim 20 comprising the further steps of repeating steps (g) and (h) until substantially all fluid from the more proximal chamber is displaced into the more distal chamber and the valved stopper is displaced proximally to abut the plunger.

22. The method for using a mixing syringe apparatus for mixing and dispensing medical fluids according to claim 21 comprising the further steps of removing the cap and applying distally directed force to dispense fluid from the syringe.

23. A method for using a mixing syringe apparatus for mixing and dispensing medical fluids according to claim 15 comprising the additional step of installing a valve assembly to divide the more proximal chamber into a more proximal chamber and a most proximal chamber.

24. The method for using a mixing syringe apparatus for mixing and dispensing medical fluids according to claim 23 comprising the steps of mixing fluids in the more proximal chamber while keeping fluid in the most proximal chamber disparate from the mixed fluids.

25. The method for using a mixing syringe apparatus for mixing and dispensing medical fluids according to claim 24 comprising the steps of dispensing each fluid from the more proximal chamber and then the fluid from the most proximal chamber sequentially.

26. A mixing syringe apparatus for mixing and dispensing medical fluids, said apparatus comprising:

a syringe comprising a conventional hollow barrel having an elongated internal cylindrical surface, said barrel surface comprising an open proximal end and a distal end having a closed interior about an orifice through which fluid is transferred, and a stem and plunger combination, said combination being disposed to be displaced within said barrel by application of force against said stem thereby imposing differential pressures for displacing fluid within the barrel; and a removable cap which, in combination with said plunger, fully confines all fluid and material previously stored within said syringe barrel between the plunger and cap;

a displaceable valved stopper disposed within said barrel between said plunger and said distal end to provide a more proximal chamber disposed between the plunger and valved stopper as a container for diluting fluid and a more distal chamber disposed between the distal end and valved stopper as a container for matter which is to be mixed and diluted with the diluent;

said displaceable valved stopper comprising;

a normally-closed valve; said valve being disposed to open to permit flow of diluting fluid there through when imposed upon by a pre-determined non-zero positive differential pressure but which closes when a predetermined non-positive differential pressure is imposed in chambers surrounding the valved stopper whereby equilibrating pressure following a positive differential pressure disposed across the valved stopper closes the valve, imposes a momentary non-positive pressure differential upon the valved stopper and thereby displaces the valved stopper proximally.

27. The mixing syringe apparatus for mixing and dispensing medical fluids according to claim 26 further comprising a non-planar slit valve.

28. A method for using a mixing syringe apparatus for mixing and dispensing medical fluids comprising the following steps:

(a) providing a syringe comprising a conventional hollow barrel having an elongated internal cylindrical surface, said barrel surface comprising an open proximal end and a distal end having a closed interior about an orifice through which fluid is transferred, and a stem and plunger combination, said combination being disposed to be displaced within said barrel by application of force against said stem thereby imposing differential pressures for displacing fluid within the barrel;

(b) providing a removable cap which, in combination with said plunger, fully confines all fluid and material previously stored within said syringe barrel between the plunger and cap;

(c) providing a displaceable valved stopper disposed within said barrel between said plunger and said distal end to provide a more proximal chamber disposed between the plunger and valved stopper as a container for a diluting fluid and a more distal chamber disposed between the distal end and valved stopper as a container for a medical material which is to be mixed with the first medical material;

said displaceable valved stopper comprising;

a normally-closed valve; said valve being disposed to open to permit flow of diluting fluid there through when imposed upon by a non-zero positive differential pressure but which closes when a non-positive differential pressure is imposed across the valved stopper whereby equilibrating pressure following a positive differential pressure disposed in chambers surrounding the valved stopper closes the valve, imposes a momentary non-positive pressure differential and thereby displaces the valved stopper proximally;

(d) placing a force on said stem to displace said stem and plunger distally from an original site relative to said barrel thereby opening the valve of the valved stopper and displacing a portion of the fluid in the more proximal chamber into the more distal chamber;

(e) releasing the force from the stem, thereby permitting the valve to close, the stem and plunger to be displaced to the original site and the valved stopper to be proximally displaced;

(f) repeating steps (d) and (e) until substantially all of the fluid originally resident in the more proximal chamber is displaced from the more proximal chamber to mix with material in the more distal chamber and the valved stopper is displaced to the abut the plunger.

* * * * *